(12) United States Patent
Lock et al.

(10) Patent No.: US 12,700,489 B2
(45) Date of Patent: Aug. 4, 2026

(54) CLOUD COACHING ARTIFICIAL INTELLIGENCE

(71) Applicant: COAPT LLC, Chicago, IL (US)

(72) Inventors: Blair Andrew Lock, Chicago, IL (US);
Levi John Hargrove, Chicago, IL (US)

(73) Assignee: COAPT LLC, Chicago, IL (US)

( * ) Notice: Subject to any disclaimer, the term of this patent is extended or adjusted under 35 U.S.C. 154(b) by 981 days.

(21) Appl. No.: 17/898,930

(22) Filed: Aug. 30, 2022

(65) Prior Publication Data

US 2024/0071595 A1 Feb. 29, 2024

(51) Int. Cl.
| | |
|---|---|
| *G16H 20/30* | (2018.01) |
| *A61F 2/70* | (2006.01) |
| *A61F 2/72* | (2006.01) |
| *G06N 5/022* | (2023.01) |
| *G09B 5/02* | (2006.01) |

(52) U.S. Cl.
CPC .............. *G16H 20/30* (2018.01); *A61F 2/72* (2013.01); *G06N 5/022* (2013.01); *G09B 5/02* (2013.01); *A61F 2002/704* (2013.01); *A61F 2002/705* (2013.01)

(58) Field of Classification Search
CPC ........ G16H 20/30; G16H 40/40; G16H 40/63; G16H 40/67; G16H 40/60; G16H 50/20; G16H 50/30; G16H 50/70; A61F 2002/704; A61F 2002/705; A61F 2/72; A61F 2/76; G06N 5/022; G06N 20/00; G06N 7/02; G09B 5/02
USPC ................. 700/254, 65; 623/24, 47; 706/12; 600/544, 545, 546, 558
See application file for complete search history.

(56) References Cited

U.S. PATENT DOCUMENTS

| | | | |
|---|---|---|---|
| 2009/0327171 A1* | 12/2009 | Tan .......................... | G06F 3/015 |
| 2019/0074093 A1* | 3/2019 | Walsh .................... | G16H 10/20 |
| 2019/0102684 A1* | 4/2019 | Beran ....................... | G06N 5/02 |
| 2019/0227627 A1* | 7/2019 | Kaifosh ............... | A61B 5/1128 |
| 2020/0074883 A1* | 3/2020 | Radovcic ................ | H04L 67/12 |
| 2020/0265948 A1* | 8/2020 | Lock ....................... | G06N 3/061 |
| 2022/0122716 A1* | 4/2022 | Sadow ............... | A61B 5/14532 |

(Continued)

FOREIGN PATENT DOCUMENTS

| | | | | |
|---|---|---|---|---|
| WO | WO-0249534 A2 * | 6/2002 | ............. | G09B 19/00 |

*Primary Examiner* — Ellis B. Ramirez
(74) *Attorney, Agent, or Firm* — MARSHALL, GERSTEIN & BORUN LLP

(57) ABSTRACT

Cloud-enabled and artificial intelligence (AI) based biosignal systems and methods are described for the coaching of users to enhance biosignal enabled devices based on device usage. The systems and methods are comprised of, and/or utilize, a cloud based server to aggregate biosignal data from biosignal enabled devices, train an enhanced AI based coaching model using the biosignal data, and to provide the enhanced AI based coaching model to the biosignal enabled devices. The biosignal enabled devices replace a first AI coaching model with the enhanced AI based coaching model, and input user-specific biosignal data to the enhanced AI based coaching model to output a device usage classification. Based on the device usage classification, the systems and methods initiate a coaching procedure that coaches the user how to use or configure the biosignal enabled device to implement an updated configuration for the biosignal enabled device that is optimized for the user.

20 Claims, 10 Drawing Sheets

(56)            References Cited

U.S. PATENT DOCUMENTS

| 2022/0198206 | A1* | 6/2022 | Hargrove | G06V 40/10 |
| 2022/0237898 | A1* | 7/2022 | Uehara | G06N 3/08 |
| 2022/0358461 | A1* | 11/2022 | Tiwari | G06N 20/00 |
| 2022/0366220 | A1* | 11/2022 | Roth | H04L 67/34 |

* cited by examiner

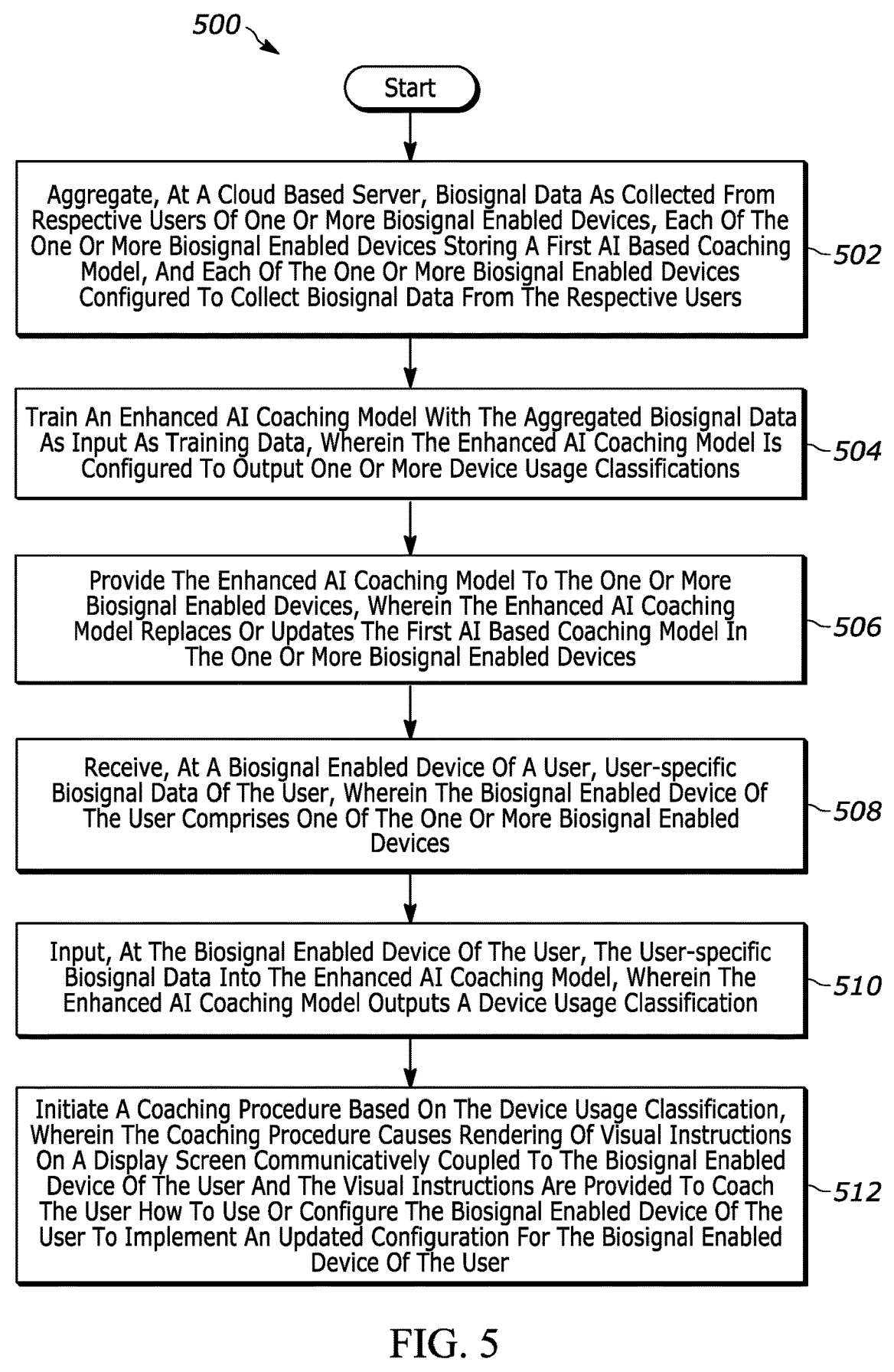

500

Start

Aggregate, At A Cloud Based Server, Biosignal Data As Collected From Respective Users Of One Or More Biosignal Enabled Devices, Each Of The One Or More Biosignal Enabled Devices Storing A First AI Based Coaching Model, And Each Of The One Or More Biosignal Enabled Devices Configured To Collect Biosignal Data From The Respective Users ~502

Train An Enhanced AI Coaching Model With The Aggregated Biosignal Data As Input As Training Data, Wherein The Enhanced AI Coaching Model Is Configured To Output One Or More Device Usage Classifications ~504

Provide The Enhanced AI Coaching Model To The One Or More Biosignal Enabled Devices, Wherein The Enhanced AI Coaching Model Replaces Or Updates The First AI Based Coaching Model In The One Or More Biosignal Enabled Devices ~506

Receive, At A Biosignal Enabled Device Of A User, User-specific Biosignal Data Of The User, Wherein The Biosignal Enabled Device Of The User Comprises One Of The One Or More Biosignal Enabled Devices ~508

Input, At The Biosignal Enabled Device Of The User, The User-specific Biosignal Data Into The Enhanced AI Coaching Model, Wherein The Enhanced AI Coaching Model Outputs A Device Usage Classification ~510

Initiate A Coaching Procedure Based On The Device Usage Classification, Wherein The Coaching Procedure Causes Rendering Of Visual Instructions On A Display Screen Communicatively Coupled To The Biosignal Enabled Device Of The User And The Visual Instructions Are Provided To Coach The User How To Use Or Configure The Biosignal Enabled Device Of The User To Implement An Updated Configuration For The Biosignal Enabled Device Of The User ~512

FIG. 5

CLOUD COACHING ARTIFICIAL INTELLIGENCE

FIELD OF THE DISCLOSURE

The present invention is generally related to the field of coaching exoprostheses users, and more specifically the coaching of these users through the usage of cloud-enabled and artificial intelligence (AI) based biosignal systems.

BACKGROUND

When initially setting up a control system for a prosthesis, it is necessary to calibrate the control based on the EMG signals produced by the user. Also, during normal daily use of a myoelectric exoprosthesis, control of the prosthesis may degrade. This degradation can occur from many different sources such as muscle exhaustion, humidity, or the prosthesis socket shifting. Because of these frequently changing variables, a myoelectric prosthesis user requires a way to regain accurate control of their device. Traditionally, when a myoelectric prosthesis user needs to have their system initially set up or recalibrated, it involves going to a prosthetist and having an in person appointment, which may take many hours to make sure that the system is correctly responding to their EMG signals. This is not always a possibility and very inconvenient for the user.

Moreover, conventional systems that enable an exoprosthetic user to calibrate/recalibrate their system independently suffer from inaccurate calibrations as a result of relatively small data sets associated with the user. Users may need to perform the calibration process multiple times to achieve a suitable calibration, and/or may simply be unable to calibrate their device on-demand until a sufficient amount of data is collected for the user. In any event, these conventional systems deprive users of suitably functioning exoprosthetics due to inaccurate calibrations.

For the foregoing reasons, there is a need for cloud-enabled and AI based biosignal systems and methods for the coaching of exoprosthetic users.

BRIEF SUMMARY

A need for the invention of the present disclosure arises from the necessity of having a method to accurately, consistently, and rapidly coach a user for successful calibration of a myoelectric prosthetic controller. The embodiments described herein describe cloud-enabled and AI based biosignal systems and methods that allow, for example, a myoelectric prosthetic user to accurately, consistently, and quickly recalibrate/configure their myoelectric prosthetic controller, without the need to go to a specialist or to wait while acquiring sufficient data of the user. In addition, the cloud-enabled and AI based biosignal systems and methods described herein allow a user to receive feedback on their calibration/configuration, which allows the user to have the most accurate control of their device. The cloud-enabled and AI based biosignal systems and methods of the present disclosure can be utilized for these, and other embodiments as described herein, as such cloud-enabled and AI based biosignal systems and methods coach the user to accurately, consistently, and quickly calibrate/configure a biosignal enabled device/system to implement an updated configuration for the biosignal enabled device of the user.

In various embodiments described herein, the biosignal enabled device may store a first AI coaching model, and the device may measure and transmit data to a cloud based server. The type of data that may be readily transmitted by the biosignal enabled device may include, for example, EMG signals, EMG features, EMG-like measurements, inertial measurement unit (IMU) signals, GPS coordinates, diagnostics information (e.g., electrode pull-off messages), information corresponding to the state of the biosignal enabled device, sensory feedback information from the exoprosthesis, calibration and control coach messages (e.g., when a user initiates calibration, which movements were calibrated, and the type of calibration (full, vs single movement)), logging information corresponding to device usage (e.g., which movements are being controlled, when and at what speed they are being controlled, interactive games are played, game scores, performance metrics, etc.). Additionally, or alternatively, the biosignal enabled device may measure and transmit data to an intermediate device (e.g., a mobile device or other computing device) which may subsequently forward the data to the cloud based server.

Regardless, the cloud based server may receive the data and may proceed to aggregate biosignal data as collected from respective users of multiple biosignal enabled devices across a network. The cloud based server may then train an enhanced AI based coaching model with the aggregated biosignal data as input as training data, wherein the enhanced AI based coaching model is configured to output one or more device usage classifications.

For example, each time a user calibrates their exoprosthesis, the data corresponding to that calibration may be transmitted to and stored in the cloud based server. The cloud based server may then apply machine-learning (ML) (e.g., deep-learning) techniques to improve the coaching model used to help advance a user's control of their exoprosthesis over time. Of course, such ML techniques may require more robust data sets for training than conventional, statically-defined algorithms. To facilitate these enhanced training data set requirements, the cloud based server may incorporate data in the training data set from multiple biosignal enabled devices that collect and transmit data from multiple users. This data may include IMU data, electrode lift-off data, and/or other data described herein, coupled with labels contextualizing what the user is trying to accomplish, to allow the cloud based server to train more robust movement models than was previously possible using conventional techniques. Thus, the enhanced AI based coaching model trained by the cloud based server may be a "globally trained" model because the training data set used to train the enhanced AI based coaching model may incorporate biosignal data from any users of biosignal enabled devices that are connected to the network, and are thereby capable of uploading biosignal data to the cloud based server.

In particular, the cloud may optimize (e.g., using a gradient descent technique) the globally trained enhanced AI based coaching model to reduce the classification error rate of the recently collected data. When the globally trained enhanced AI based coaching model reaches a sufficiently low classification error rate, the cloud based server may push a message to the user's biosignal enabled device notifying them that they have an updated model to try on the device. The user may then utilize the enhanced AI based coaching model to receive a device usage classification, which may initiate a coaching procedure based on the device usage classification. The coaching procedure may cause rendering of visual instructions on a display screen communicatively coupled to the biosignal enabled device of the user, and the user may receive visual (and/or audio) instructions intended to coach the user how to use or configure the biosignal enabled device. As a result of the coaching procedure, the user may implement an updated configuration for the biosignal enabled device.

The representative embodiments of the present invention provide numerous advantages over the commonly used methods of calibrating/configuring biosignal enabled devices/systems. The general purpose of the invention is to provide a method for accurate, consistent, and quick recalibration and training of a biosignal enabled device/system. In various embodiments, the many novel features described herein result in a new method for accurately, consistently, and rapidly coaching the user through successful calibration/configuration procedures for the user's biosignal enabled device/system.

To attain this, the present invention generally comprises a cloud-enabled and artificial intelligence (AI) based biosignal system configured to enhance biosignal enabled devices based on device usage. The cloud-enabled and artificial intelligence biosignal system may comprise: one or more biosignal enabled devices, each of the one or more biosignal enabled devices comprising a device processor and a device memory storing a first AI based coaching model, and each of the one or more biosignal enabled devices configured to collect biosignal data from respective users; server computing instructions configured for execution on a cloud based server comprising a server processor and a server memory, wherein the cloud based server is communicatively coupled to the one or more biosignal enabled devices, wherein the server computing instructions, when executed by the server processor, cause the server processor to: aggregate biosignal data as collected from respective users of the one or more biosignal enabled devices, train an enhanced AI based coaching model with the aggregated biosignal data as input as training data, wherein the enhanced AI based coaching model is configured to output one or more device usage classifications, and provide the enhanced AI based coaching model to the one or more biosignal enabled devices, wherein the enhanced AI based coaching model replaces or updates the first AI based coaching model in the device memory of the one or more biosignal enabled devices; and device computing instructions configured for execution by a respective device processor communicatively coupled to a biosignal enabled device of a user, the biosignal enabled device of the user comprising one of the one or more biosignal enabled devices, and wherein the device computing instructions as stored in a respective device memory of the biosignal enabled device of the user, when executed by the respective device processor, causes the respective device processor to: receive user-specific biosignal data of the user, input the user-specific biosignal data into the enhanced AI based coaching model, wherein the enhanced AI based coaching model outputs a device usage classification, and initiate a coaching procedure based on the device usage classification, wherein the coaching procedure causes rendering of visual instructions on a display screen communicatively coupled to the biosignal enabled device of the user, wherein the visual instructions are provided to coach the user how to use or configure the biosignal enabled device of the user to implement an updated configuration for the biosignal enabled device of the user.

In additional embodiments, the present invention may comprise a cloud-enabled and artificial intelligence (AI) based biosignal method for enhancing biosignal enabled devices based on device usage. The cloud-enabled and artificial intelligence biosignal method may comprise: aggregating, at a cloud based server comprising a server processor and a server memory, biosignal data as collected from respective users of one or more biosignal enabled devices, each of the one or more biosignal enabled devices comprising a device processor and a device memory storing a first AI based coaching model, and each of the one or more biosignal enabled devices configured to collect biosignal data from the respective users; training an enhanced AI based coaching model with the aggregated biosignal data as input as training data, wherein the enhanced AI based coaching model is configured to output one or more device usage classifications; providing the enhanced AI based coaching model to the one or more biosignal enabled devices, wherein the enhanced AI based coaching model replaces or updates the first AI based coaching model in the device memory of the one or more biosignal enabled devices; receiving, at a biosignal enabled device of a user, user-specific biosignal data of the user, wherein the biosignal enabled device of the user comprises one of the one or more biosignal enabled devices; inputting, at the biosignal enabled device of the user, the user-specific biosignal data into the enhanced AI based coaching model, wherein the enhanced AI based coaching model outputs a device usage classification; and initiating a coaching procedure based on the device usage classification, wherein the coaching procedure causes rendering of visual instructions on a display screen communicatively coupled to the biosignal enabled device of the user, wherein the visual instructions are provided to coach the user how to use or configure the biosignal enabled device of the user to implement an updated configuration for the biosignal enabled device of the user.

In additional embodiments, the present invention may comprise a tangible, non-transitory computer-readable medium storing instructions for enhancing biosignal enabled devices based on device usage, that when executed by one or more processors cause the one or more processors to: aggregate, at a cloud based server comprising a server processor and a server memory, biosignal data as collected from respective users of one or more biosignal enabled devices, each of the one or more biosignal enabled devices comprising a device processor and a device memory storing a first AI based coaching model, and each of the biosignal enabled devices configured to collect biosignal data from the respective users; train an enhanced AI based coaching model with the aggregated biosignal data as input as training data, wherein the enhanced AI based coaching model is configured to output one or more device usage classifications; provide the enhanced AI based coaching model to the one or more biosignal enabled devices, wherein the enhanced AI based coaching model replaces or updates the first AI based coaching model in the device memory of the one or more biosignal enabled devices; receive, at a biosignal enabled device of a user, user-specific biosignal data of the user, wherein the biosignal enabled device of the user comprises one of the one or more biosignal enabled devices; input, at the biosignal enabled device of the user, the user-specific biosignal data to the enhanced AI based coaching model, wherein the enhanced AI based coaching model outputs a device usage classification; and initiate a coaching procedure based on the device usage classification, wherein the coaching procedure causes rendering of visual instructions on a display screen communicatively coupled to the biosignal enabled device of the user, wherein the visual instructions are provided to coach the user how to use or configure the biosignal enabled device of the user to implement an updated configuration for the biosignal enabled device of the user.

In accordance with the above, and with the disclosure herein, the present disclosure includes improvements in computer functionality or in improvements to other technologies at least because the present disclosure describes that, e.g., prosthetic devices, and their related various components, may be improved or enhanced with the disclosed cloud-enabled and AI based biosignal systems and methods that provide more accurate, consistent, and efficient calibration and control of the prosthetic devices for their respective users. That is, the present disclosure describes improvements in the functioning of a prosthetic device itself or "any other technology or technical field" (e.g., the field of electromyography and biosignal systems) because the disclosed cloud-enabled and AI based biosignal systems and methods improve and enhance operation, and reduce error rate, of prosthetic devices by introducing improved recalibration procedures for correcting non-optimal EMG biosignal data to eliminate errors and malfunctions typically experienced over time by prosthetic devices lacking such systems and methods. This improves over the prior art at least because such previous systems were error-prone as they lack the ability for accurately, consistently, or rapidly coaching the user through a successful calibration procedure for the user's biosignal control systems.

In addition, the present disclosure includes applying various features and functionality, as described herein, with, or by use of, a particular machine, e.g., a biosignal enabled device, a cloud based server, a prosthetic device, a button, and/or other hardware components as described herein.

Moreover, the present disclosure includes effecting a transformation or reduction of a particular article to a different state or thing, e.g., transforming or reducing the calibration and/or operation of a prosthetic device from a non-optimal or error state to an optimal or calibrated state.

Still further, the present disclosure includes specific features other than what is well-understood, routine, conventional activity in the field, or adding unconventional steps that demonstrate, in various embodiments, particular useful applications, e.g., cloud-enabled and AI based biosignal systems and methods for the coaching of exoprosthetic users.

Advantages will become more apparent to those of ordinary skill in the art from the following description of the preferred embodiments, which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The objects, features and advantages of the present invention and additional embodiments will be more readily appreciated upon reference to the following disclosure when considered in conjunction with the accompanying drawings, wherein like reference numerals are used to identify identical components in the various views.

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

Figure 1:
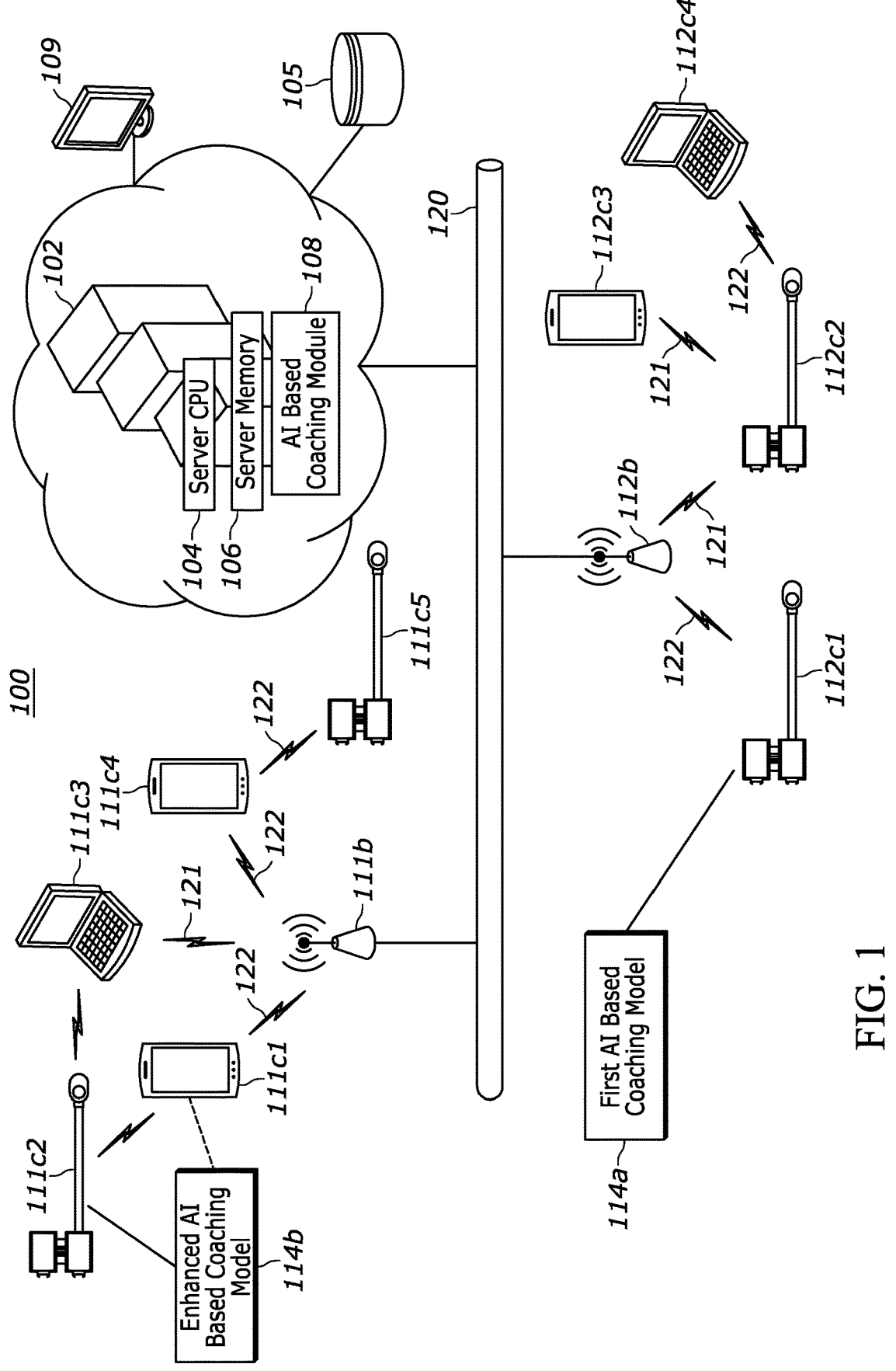

There are shown in the drawings arrangements which are presently discussed, it being understood, however, that the present embodiments are not limited to the precise arrangements and instrumentalities shown, wherein:

FIG. 1 illustrates an example computing environment in which cloud-enabled and AI based biosignal systems for enhancing biosignal enabled devices based on device usage may be implemented, in accordance with various embodiments disclosed herein.

Figure 2A:
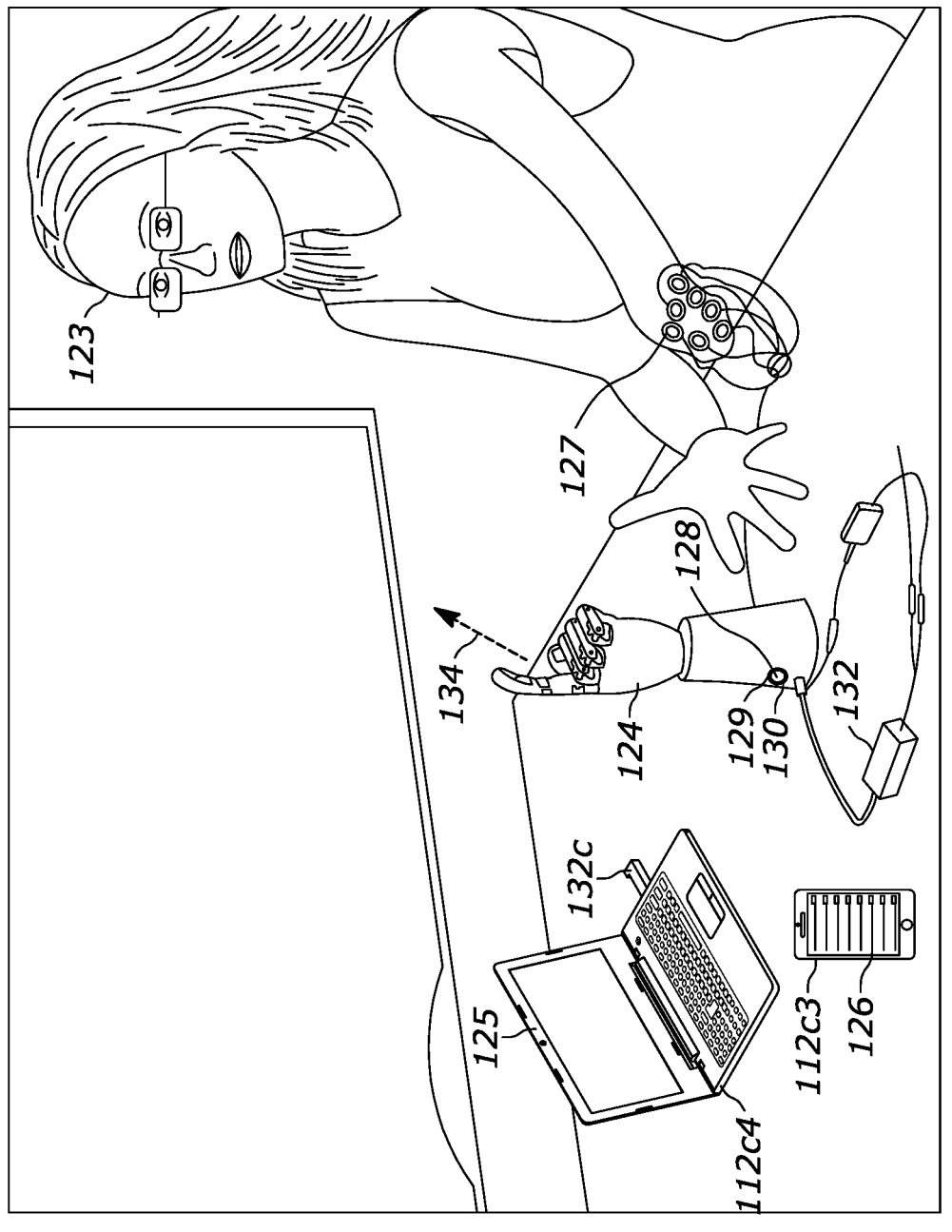

FIG. 2A illustrates an example representation of a user with a prosthetic wrist and hand with electrodes and components of the example computing environment of FIG. 1, along with separate modalities for accessing a virtual user interface, and in accordance with various embodiments disclosed herein.

Figure 2B:
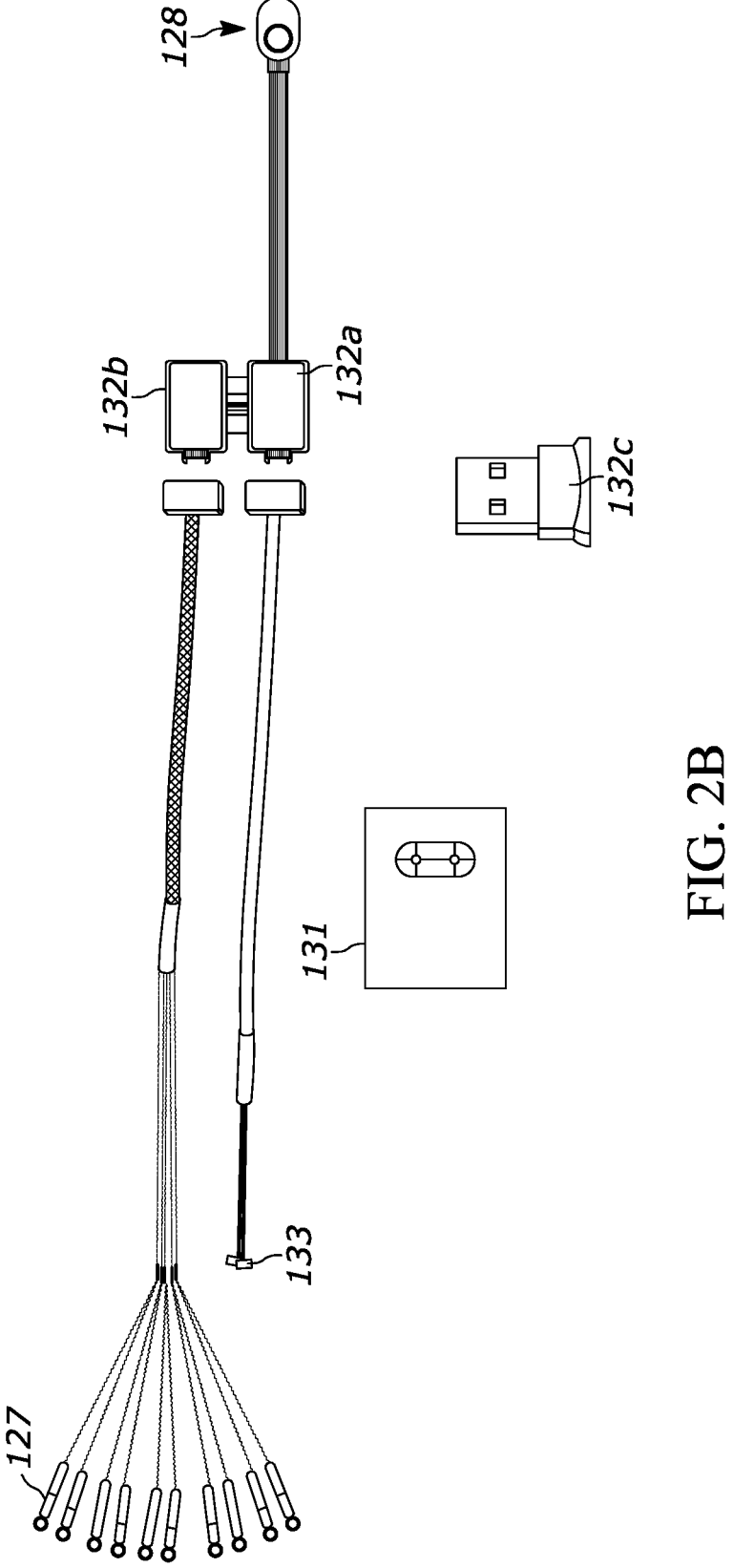
Figure 3A:
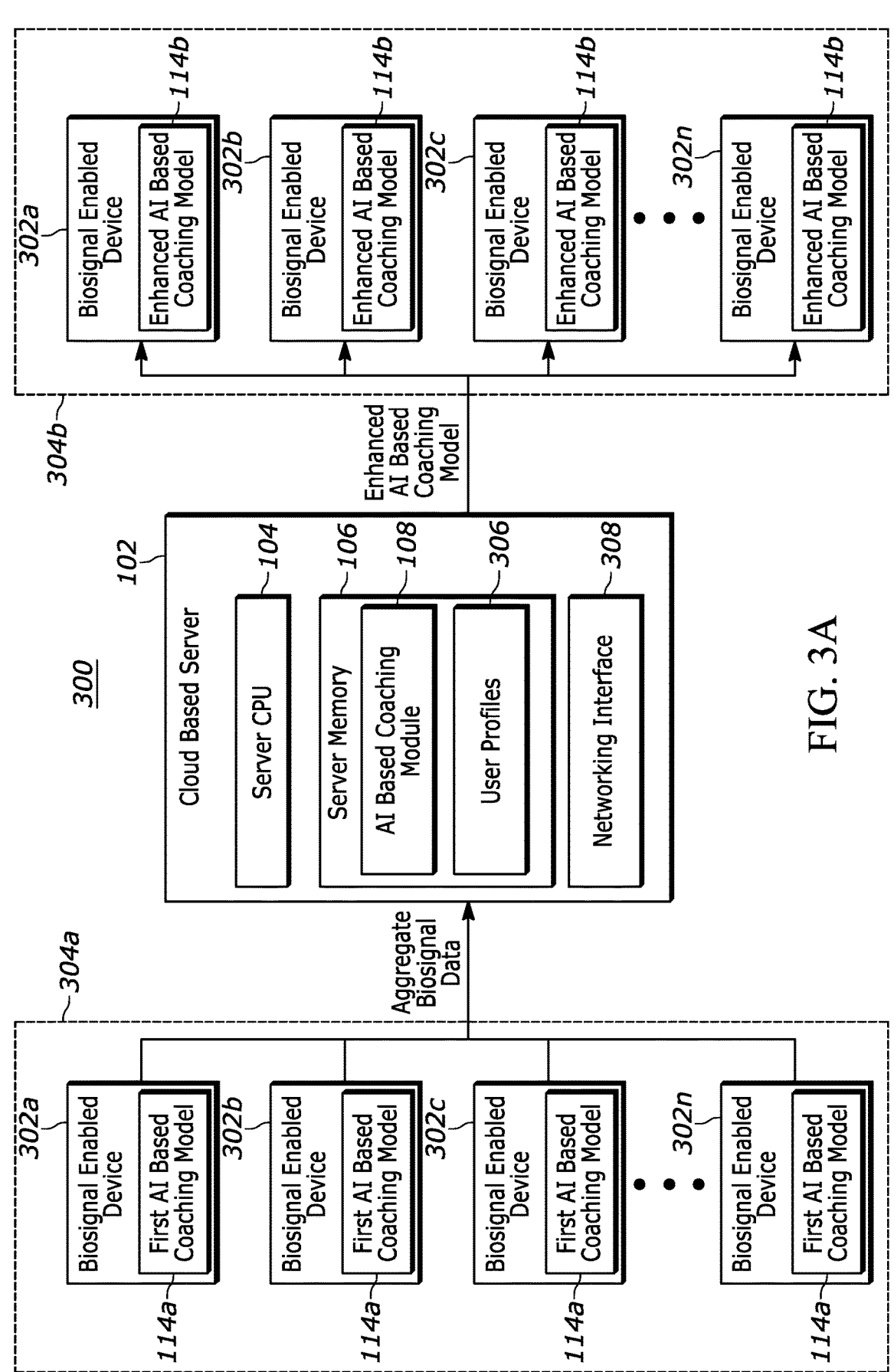

FIG. 2B illustrates an alternative embodiment of the button and the plurality of electrodes of FIG. 2A, in accordance with various embodiments disclosed herein FIG. 3A is a block diagram representing training performed by the cloud based server of FIG. 1 in order to train the enhanced AI based coaching model, in accordance with various embodiments disclosed herein.

Figure 3B:
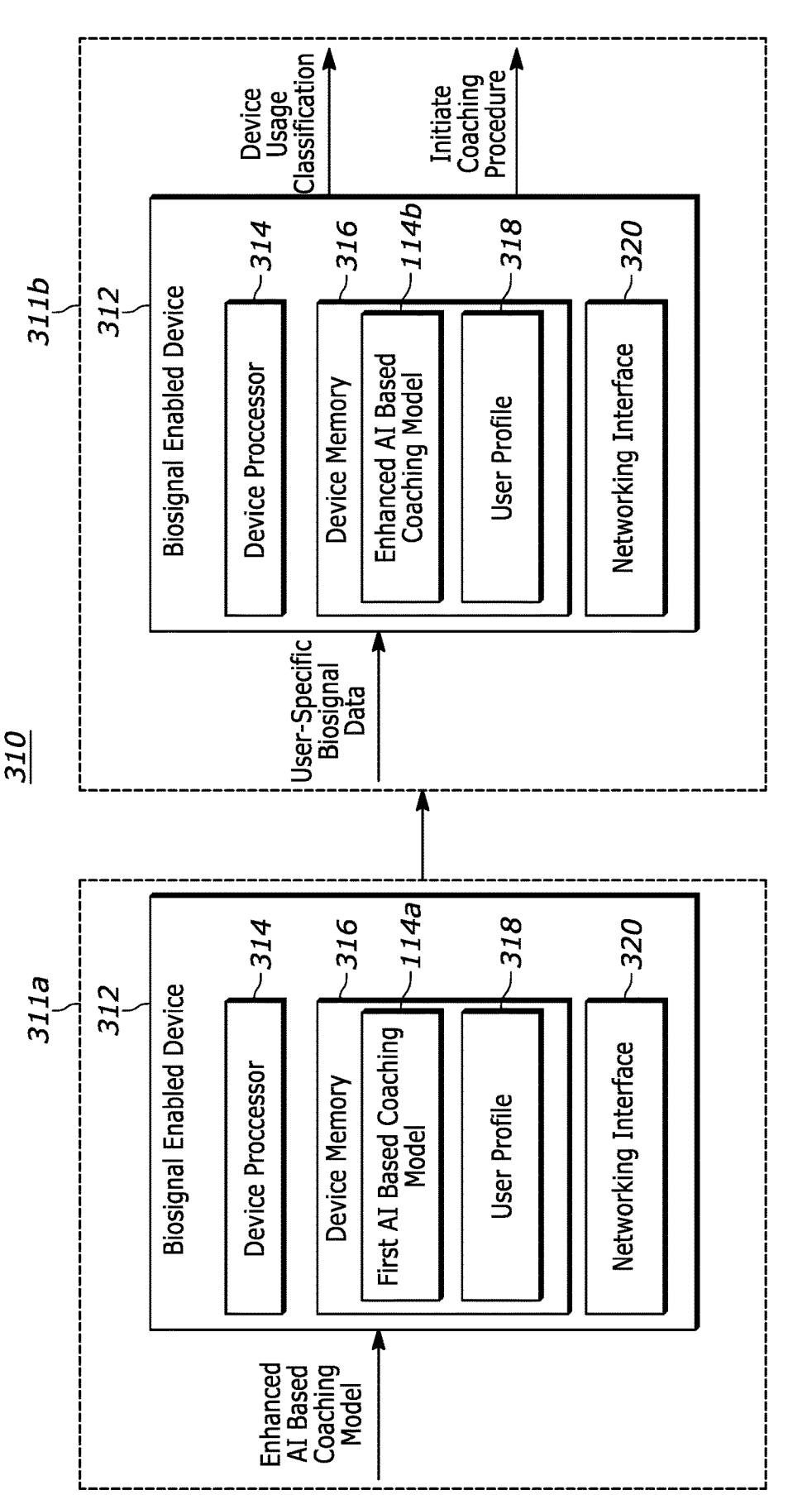

FIG. 3B is a block diagram representing data input and output to/from a biosignal enabled device of FIGS. 1, 2A, and 3A, including the enhanced AI based coaching model of FIG. 3A, to initiate a coaching procedure for a user, and in accordance with various embodiments disclosed herein.

Figure 3C:
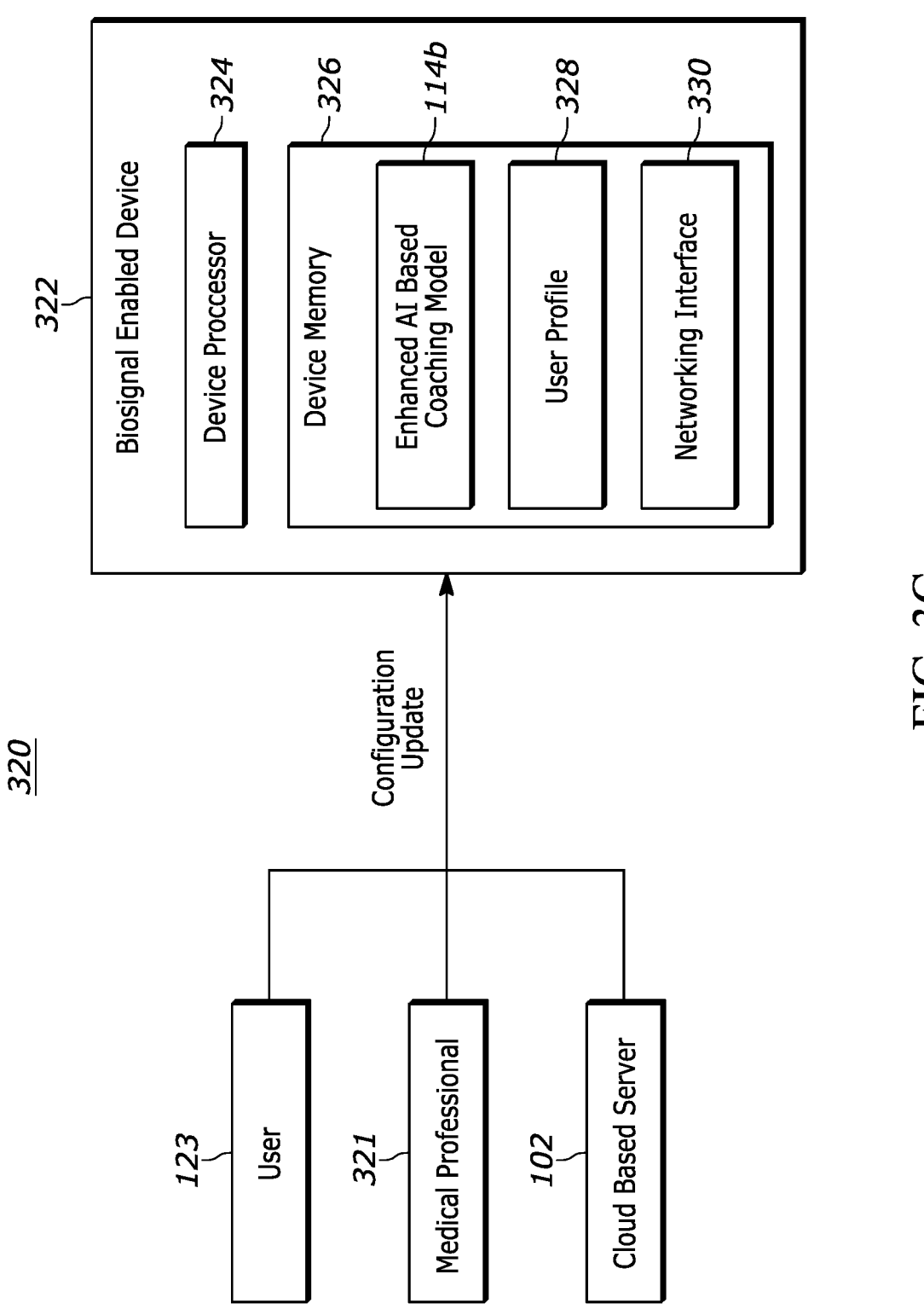

FIG. 3C is a block diagram representing data input and output to/from the biosignal enabled device of FIGS. 1 and 2A to modify an operation configuration of the biosignal enabled device, in accordance with various embodiments disclosed herein.

Figure 4A:
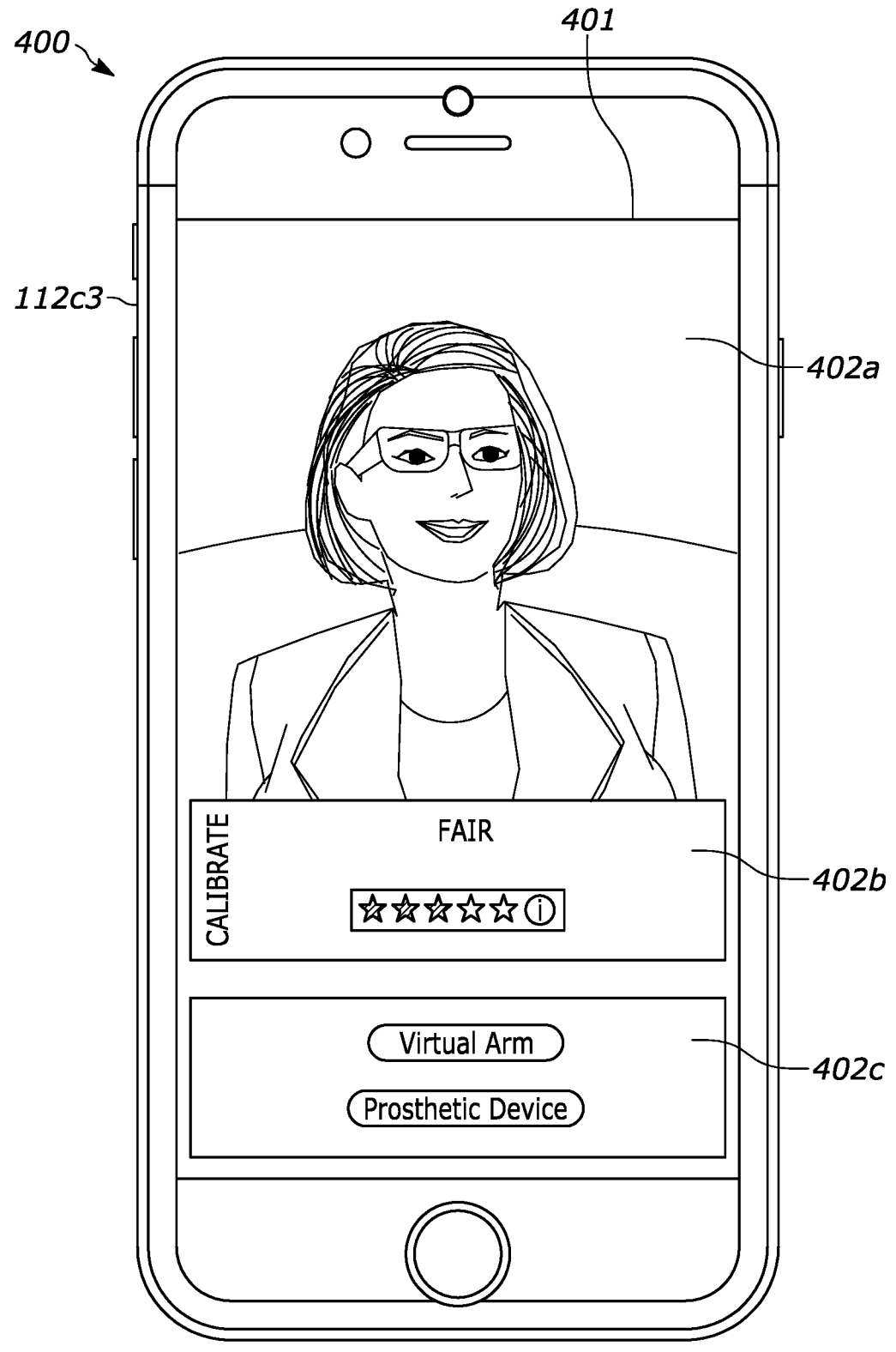

FIG. 4A illustrates an example specialist portal graphical user interface (GUI) rendered on a display screen of a user computing device communicatively coupled to the biosignal enabled device, the example specialist GUI configured to provide access to a medical professional to read, modify, or provide coaching instructions to the user, and in accordance with various embodiments disclosed herein.

Figure 4B:
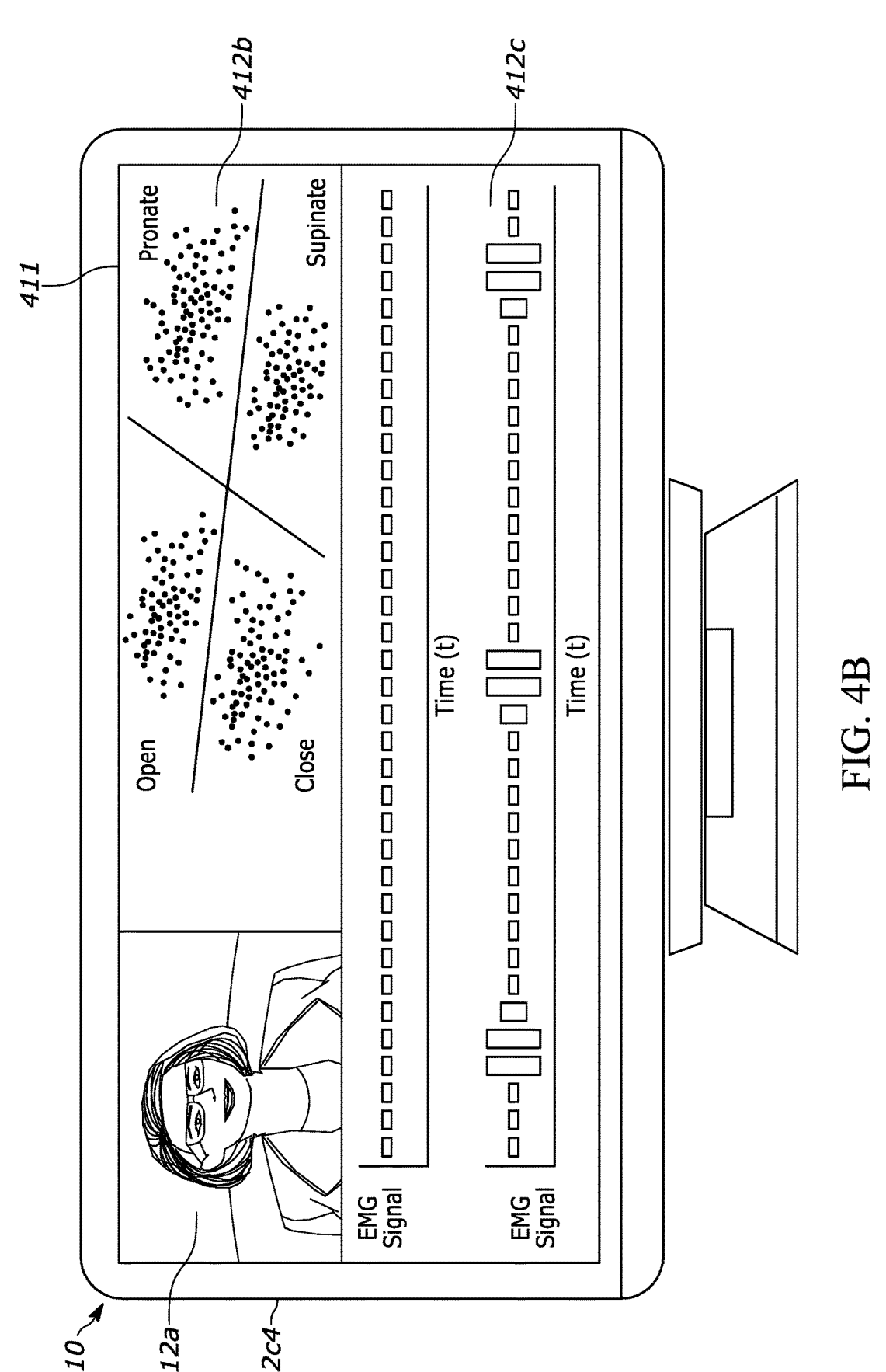

FIG. 4B illustrates another example specialist GUI rendered on a display screen of another user computing device communicatively coupled to the biosignal enabled device, in accordance with various embodiments disclosed herein.

Figure 4C:
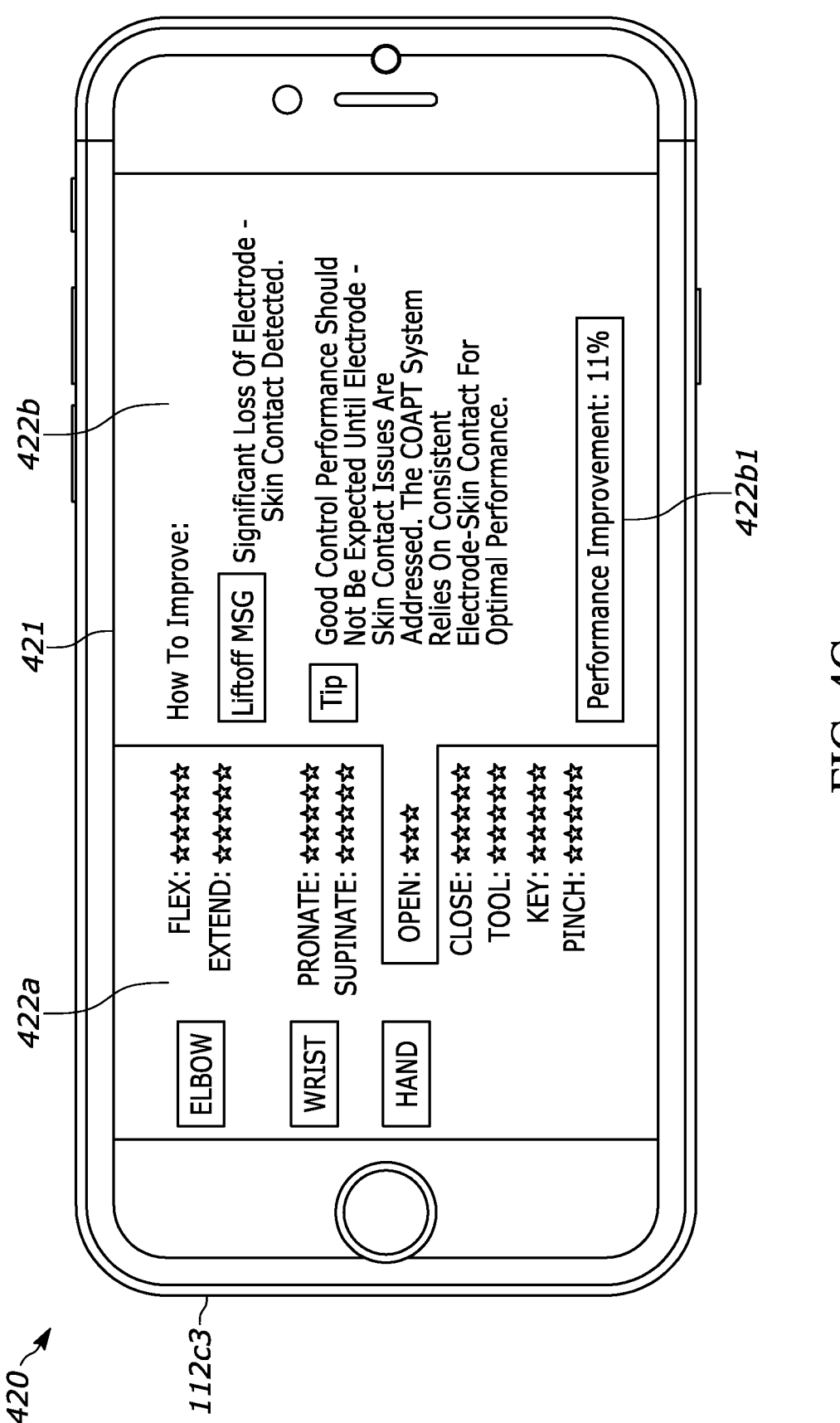

FIG. 4C illustrates an example GUI configured to display performance metrics indicating performance improvement of a user's biosignal enabled device as a result of coaching the user to configure the biosignal enabled device based on the device classification output by the enhanced AI based coaching model of FIGS. 1 and 3A-3C, and in accordance with various embodiments disclosed herein.

FIG. 5 is a block diagram flowchart representing an example cloud-enabled and AI based biosignal method for enhancing biosignal enabled devices based on device usage, in accordance with various embodiments disclosed herein.

The Figures depict preferred embodiments for purposes of illustration only. Alternative embodiments of the systems and methods illustrated herein may be employed without departing from the principles of the invention described herein.

DETAILED DESCRIPTION

While the present invention is susceptible of embodiment in many different forms, there are shown in the drawings and will be described herein in detail specific exemplary embodiments thereof, with the understanding that the present disclosure is to be considered as an exemplification of the principles of the invention and is not intended to limit the invention to the specific embodiments illustrated. Methods and apparatuses consistent with the present invention are capable of other embodiments and of being practiced and carried out in various ways. Also, it is to be understood that the phraseology and terminology employed herein, as well as the abstract included below, are for the purposes of description and should not be regarded as limiting.

As disclosed in various embodiments herein, a cloud-enabled and AI based biosignal system is described for the coaching of exoprosthetic users. The cloud-enabled and AI based biosignal system may also be referred to herein as "the system." The system is generally comprised of hardware and software components configured to input and analyze various data (e.g., EMG based signals) in association with movements of a user, and to coach the user to configure/calibrate a biosignal enabled device based on the data. For example, the data may be user-specific biosignal data that may include EMG signals, EMG features, EMG-like measurements, inertial measurement unit (IMU) signals, GPS coordinates, diagnostics information (e.g., electrode pull-off messages), information corresponding to the state of the biosignal enabled device, sensory feedback information from the exoprosthesis, calibration and control coach messages (e.g., when a user initiates calibration, which movements were calibrated, and the type of calibration (full, vs single movement)), logging information corresponding to device usage (e.g., which movements are being controlled, when and at what speed they are being controlled, interactive games are played, game scores, performance metrics, etc.). The cloud-enabled and AI based biosignal system, and portions thereof, including its various hardware and software components, are illustrated herein by the provided Figures.

In particular, FIG. 1 illustrates an example computing environment in which a cloud-enabled and AI based biosignal system 100 for enhancing biosignal enabled devices (e.g., devices 111c2, 111c5, 112c1, 112c2) based on device usage may be implemented, in accordance with various embodiments disclosed herein. In the example computing environment of FIG. 1, the AI based biosignal system 100 includes server(s) 102, which may comprise one or more computer servers. In various aspects, the server(s) 102 comprise multiple servers, which may comprise multiple, redundant, or replicated servers as part of a server farm. In still further aspects, the server(s) 102 may be implemented as cloud based servers, such as a cloud based computing platform. For example, the server(s) 102 may be any one or more cloud based platform(s) such as MICROSOFT AZURE, AMAZON AWS, or the like. The server(s) 102 may include one or more server processor(s) 104, one or more server memories 106, and an AI based coaching module 108.

The server memories 106 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. The server memories 106 may store an operating system (OS) (e.g., Microsoft Windows, Linux, UNIX, etc.) capable of facilitating the functionalities, apps, methods, or other software as discussed herein. The server memories 106 may also store the AI based coaching module 108, which may be a module configured to train one or more machine learning models, such as a first AI based coaching model 114a and/or the enhanced AI based coaching model 114b. In various aspects, the AI based coaching module 108 may comprise computing instructions configured to be executed by one or more processor(s) (e.g., CPU 104) of server(s) 102. In particular, the AI based coaching module 108, being executed by one or processor(s), may train the machine learning models using various training data (e.g., potentially thousands of instances (or more) of user-specific/aggregate biosignal data regarding biosignal data of respective individuals using/calibrating/configuring their respective biosignal enabled devices), as described herein. Additionally, or alternatively, the server(s) 102 may store any trained AI based coaching models 114a, 114b in a database 105, which is accessible or otherwise communicatively coupled to the server(s) 102.

In addition, the server memories 106 may also store machine readable instructions, including any of one or more application(s) (e.g., a specialist portal application as described herein), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For example, at least some of the applications, software components, or APIs may be, include, otherwise be part of, an AI based coaching module, model, or component, such as the AI based coaching module 108, where each may be configured to facilitate their various functionalities discussed herein. It should be appreciated that one or more other applications may be envisioned and that are executed by the server processors 104.

The server processors 104 may be connected to the server memories 106 via a computer bus responsible for transmitting electronic data, data packets, or otherwise electronic signals to and from the server processors 104 and the server memories 106 in order to implement or perform the machine readable instructions, methods, processes, elements or limitations, as illustrated, depicted, or described for the various flowcharts, illustrations, diagrams, figures, and/or other disclosure herein.

The server processors 104 may interface with the server memories 106 via the computer bus to execute an operating system (OS). The server processors 104 may also interface with the server memories 106 via the computer bus to create, read, update, delete, or otherwise access or interact with the data stored in the server memories 106 and/or the database 105 (e.g., a relational database, such as Oracle, DB2, MySQL, or a NoSQL based database, such as MongoDB). The data stored in the server memories 106 and/or the database 105 may include all or part of any of the data or information described herein, including, for example, training data (e.g., as collected by the biosignal enabled devices 111c2, 111c5, 112c1, and/or 112c2); and/or other information of the user, including information related to demographics, age, or the like, and/or as otherwise described herein.

The server(s) 102 may further include a communication component configured to communicate (e.g., send and receive) data via one or more external/network port(s) to one or more networks or local terminals, such as computer network 120 and/or terminal 109 (for rendering or visualizing) described herein. In some aspects, the server(s) 102 may include a client-server platform technology such as ASP.NET, Java J2EE, Ruby on Rails, Node.js, a web service or online API, responsive for receiving and responding to electronic requests. The server(s) 102 may implement the client-server platform technology that may interact, via the computer bus, with the server memories 106 (including the applications(s), component(s), API(s), data, etc. stored therein) and/or the database 105 to implement or perform the machine readable instructions, methods, processes, elements or limitations, as illustrated, depicted, or described for the various flowcharts, illustrations, diagrams, figures, and/or other disclosure herein.

In various aspects, the server(s) 102 may include, or interact with, one or more transceivers (e.g., WWAN, WLAN, and/or WPAN transceivers) functioning in accordance with IEEE standards, 3GPP standards, or other standards, and that may be used in receipt and transmission of data via external/network ports connected to the computer network 120. In some aspects, the computer network 120 may comprise a private network or local area network (LAN). Additionally, or alternatively, the computer network 120 may comprise a public network such as the Internet.

The server(s) 102 may further include or implement an operator interface configured to present information to an administrator or operator and/or receive inputs from the administrator or operator. As shown in FIG. 1, an operator interface may provide a display screen (e.g., via terminal 109). The server(s) 102 may also provide I/O components (e.g., ports, capacitive or resistive touch sensitive input panels, keys, buttons, lights, LEDs), which may be directly accessible via, or attached to, the server(s) 102 or may be indirectly accessible via or attached to the terminal 109. According to some aspects, an administrator or operator may access the server(s) 102 via the terminal 109 to review information, make changes, input training data, initiate training actions of the AI based coaching module 108, and/or perform other functions.

As described herein, in some aspects, the server(s) 102 may perform the functionalities as discussed herein as part of a "cloud" network or may otherwise communicate with other hardware or software components within the cloud to send, retrieve, or otherwise analyze data or information described herein.

In general, a computer program or computer based product, application, or code (e.g., the AI based coaching module 108, or other computing instructions described herein) may be stored on a computer usable storage medium, or tangible, non-transitory computer-readable medium (e.g., standard random access memory (RAM), an optical disc, a universal serial bus (USB) drive, or the like) having such computer-readable program code or computer instructions embodied therein, wherein the computer-readable program code or computer instructions may be installed on or otherwise adapted to be executed by the server processors 104 (e.g., working in connection with the respective operating system in the server memories 106) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C #, Objective-C, Java, Scala, ActionScript, JavaScript, HTML, CSS, XML, etc.).

As shown in FIG. 1, the server(s) 102 are communicatively connected, via the computer network 120 to the one or more user computing devices 111$c1$, 111$c3$, 111$c4$, 112$c3$, and/or 112$c4$ and the biosignal enabled devices 112$c2$, 111$c5$, 112$c1$, and/or 112$c2$ via base stations 111$b$ and 112$b$.

In some aspects, base stations 111$b$ and 112$b$ may comprise cellular base stations, such as cell towers, communicating to the one or more user computing devices 111$c1$, 111$c3$, 111$c4$, 112$c3$, and/or 112$c4$ and/or the biosignal enabled devices 112$c2$, 111$c5$, 112$c1$, and/or 112$c2$ via wireless communications 121 based on any one or more of various mobile phone standards, including NMT, GSM, CDMA, UMMTS, LTE, 5G, or the like.

Additionally, or alternatively, base stations 111$b$ and 112$b$ may comprise routers, wireless switches, or other such wireless connection points communicating to the one or more user computing devices 111$c1$, 111$c3$, 111$c4$, 112$c3$, and/or 112$c4$ and/or the biosignal enabled devices 112$c2$, 111$c5$, 112$c1$, and/or 112$c2$ via wireless communications 122 based on any one or more of various wireless standards, including by non-limiting example, IEEE 802.11a/b/c/g (WIFI), the BLUETOOTH standard, or the like.

Any of the one or more user computing devices 111$c1$, 111$c3$, 111$c4$, 112$c3$, and/or 112$c4$ may comprise mobile devices and/or client computing devices (e.g., laptop computers, desktop computers, etc.) for accessing and/or communications with the server(s) 102. In various aspects, user computing devices 111$c1$, 111$c3$, 111$c4$, 112$c3$, and/or 112$c4$ may comprise a mobile phone (e.g., a cellular phone), a tablet device, a personal data assistance (PDA), or the like, including, by non-limiting example, an APPLE iPhone or iPad device or a GOOGLE ANDROID based mobile phone or table.

The biosignal enabled devices 112$c2$, 111$c5$, 112$c1$, and/or 112$c2$ may generally comprise and/or otherwise include controllers (not shown) configured to control prosthetic devices (not shown) of respective users. More specifically, the biosignal enabled devices 112$c2$, 111$c5$, 112$c1$, and/or 112$c2$ may receive user-specific biosignal data from the user's prosthetic device that is representative of a user's control, calibration, and/or otherwise interactions with the user's prosthetic device. The biosignal enabled devices 112$c2$, 111$c5$, 112$c1$, and/or 112$c2$ may then apply AI coaching models (e.g., 114$a$, 114$b$) to determine a device usage classification associated with the user's prosthetic device, so that the devices 112$c2$, 111$c5$, 112$c1$, and/or 112$c2$ may then initiate a coaching procedure for the user to calibrate their controller to improve the user's control of the prosthetic device. In this manner, users may autonomously calibrate the controllers of their prosthetic devices using the AI coaching models 114$a$, 114$b$ stored on the biosignal enabled devices 112$c2$, 111$c5$, 112$c1$, and/or 112$c2$, and can thereby avoid the hassle of visiting a prosthetist to calibrate the controller in the conventional way.

Additionally, the biosignal enabled devices 112$c2$, 111$c5$, 112$c1$, and/or 112$c2$ may periodically receive enhanced AI based coaching models (e.g., enhanced AI based coaching model 114$b$) from the server(s) 102 to update older AI based coaching models (e.g., first AI based coaching model 114$a$). The server(s) 102 may aggregate biosignal data from multiple users who have biosignal enabled devices (e.g., 112$c2$, 111$c5$, 112$c1$, and/or 112$c2$) connected to the computer network 120, and the AI based coaching module 108 may use the aggregate biosignal data to train an enhanced AI based coaching model 114$b$. The server(s) 102 may then push the enhanced AI based coaching model 114$b$ to each connected biosignal enabled device 112$c2$, 111$c5$, 112$c1$, and/or 112$c2$ in order to replace the first AI based coaching model 114$a$ with the enhanced AI based coaching model 114$b$. Thus, as illustrated in FIG. 1, the biosignal enabled device 111$c2$ may have received the enhanced AI based coaching model 114$b$ from the server(s) 102, but the biosignal enabled device 112c1 may not have received the enhanced AI based coaching model 114b yet from the server(s) 102 to replace the first AI based coaching model 114a.

In any event, each biosignal enabled device 112c2, 111c5, 112c1, and/or 112c2 may include device processors (not shown), device memories (not shown), networking interfaces (not shown), and/or other components or subcomponents thereof that may configure the devices 112c2, 111c5, 112c1, and/or 112c2 to implement/execute AI based coaching models (e.g., 114a, 114b), communicate with external devices (e.g., server(s) 102, one or more user computing devices 111c1, 111c3, 111c4, 112c3, and/or 112c4), and/or any other functions or combinations thereof, as described herein. Additionally, or alternatively, the biosignal enabled devices 112c2, 111c5, 112c1, and/or 112c2 may be wearable devices, such that a user may wear the biosignal enabled device 112c2, 111c5, 112c1, and/or 112c2 along with their respective prosthetic device.

In various aspects, the one or more user computing devices 111c1, 111c3, 111c4, 112c3, and/or 112c4 may implement or execute an operating system (OS) or mobile platform such as APPLE's iOS and/or GOOGLE's ANDROID operation system. Any of the one or more user computing devices 111c1, 111c3, 111c4, 112c3, and/or 112c4 may comprise one or more processors and/or one or more memories for storing, implementing, or executing computing instructions or code, e.g., a mobile application or a specialist portal application, as described in various aspects herein. As shown in FIG. 1, the AI based coaching models 114a, 114b, and/or a calibration application and/or specialist portal application, as described herein, or at least portions thereof, may also be stored locally on a memory of a user computing device (e.g., user computing device 111c1).

User computing devices 111c1, 111c3, 111c4, 112c3, and/or 112c4 and/or the biosignal enabled devices 112c2, 111c5, 112c1, and/or 112c2 may comprise a wireless transceiver to receive and transmit wireless communications 121 and/or 122 to and from base stations 111b and/or 112b. Further, the user computing devices 111c1, 111c3, 111c4, 112c3, and/or 112c4 and/or the biosignal enabled devices 112c2, 111c5, 112c1, and/or 112c2 may transmit user-specific biosignal data (e.g., EMG signals, IMU signals, GPS coordinates, device state information, diagnostic data, etc.) via the computer network 120 to the server(s) 102 for training of model(s) (e.g., enhanced AI based coaching model 114b) by the AI based coaching module 108 and/or analysis as described herein.

Still further, each of the one or more user computer devices 111c1, 111c3, 111c4, 112c3, and/or 112c4 and/or the biosignal enabled devices 112c2, 111c5, 112c1, and/or 112c2 may include a display screen for displaying graphics, images, text, a specialist portal, virtual instructions, performance metrics, user-specific biosignal data, pixels, features, and/or other such visualizations or information as described herein. In various aspects, graphics, images, text, a specialist portal, virtual instructions, performance metrics, user-specific biosignal data, pixels, features, and/or other such visualizations or information may be received from the server(s) 102 for display on the display screen of any one or more of the one or more user computer devices 111c1, 111c3, 111c4, 112c3, and/or 112c4 and/or the biosignal enabled devices 112c2, 111c5, 112c1, and/or 112c2. Additionally, or alternatively, any of the one or more user computer devices 111c1, 111c3, 111c4, 112c3, and/or 112c4 and/or the biosignal enabled devices 112c2, 111c5, 112c1, and/or 112c2 may comprise, implement, have access to, render, or otherwise expose, at least in part, an interface or a graphical user interface (GUI) for displaying text and/or images on its display screen.

In some aspects, computing instructions and/or applications executing at the server(s) 102 and/or at the one or more user computer devices 111c1, 111c3, 111c4, 112c3, and/or 112c4 and/or the biosignal enabled devices 112c2, 111c5, 112c1, and/or 112c2 may be communicatively connected for analyzing user-specific biosignal data, as described herein. For example, the server processors 104 may be communicatively coupled to one or more user computer devices 111c1, 111c3, 111c4, 112c3, and/or 112c4 and/or the biosignal enabled devices 112c2, 111c5, 112c1, and/or 112c2 via the computer network 120.

FIG. 2A illustrates an example representation of a user 123 with a prosthetic wrist and hand (e.g., prosthetic device 124) with electrodes 127 and components of the example computing environment of FIG. 1, along with separate modalities for accessing a virtual user interface 125, 126, and in accordance with various embodiments disclosed herein. Namely, FIG. 2A illustrates two separate modalities for accessing the virtual user interfaces 125, 126, as rendered on the display screens of the user computing device 112c4 and the user computing device 112c3, respectively, of FIG. 1. Moreover, FIG. 2A illustrates a connection module 132 that may connect the electrodes 122 to the prosthetic device 124, and in certain instances, may include a biosignal enabled device (e.g., biosignal enabled devices 112c2, 111c5, 112c1, 112c2) configured to receive user-specific biosignal data from the electrodes 127 and/or the prosthetic device 124.

Each of the plurality of electrodes 127 and the user computing devices 112c3, 112c4 may be communicatively coupled to a prosthetic device 124. For example, the plurality of electrodes 127 and the user computing devices 112c3, 112c4 may be communicatively coupled to the prosthetic device 124 via wired or wireless hardware and/or software components (e.g., via connection module 132, UI 125, mobile application-based UI 126, etc.). In various embodiments, the plurality of electrodes 127 may be configured as EMG electrodes. In this manner, the plurality of electrodes 127 may transmit biosignal data from a limb or other attachment point of the user 123 to the connection module 132, where the biosignal data may be interpreted and converted into control instructions to control the prosthetic device 124. This biosignal data transmitted by the plurality of electrodes 127 may indicate, define, or classify movements of the user 123 over time (e.g., EMG biosignal data of movements) as any one or more of, for example, "inconsistent," "liftoff," "noisy," "quiet," "indistinct," "similar," "early," "late," "weak," "strong," and/or any other suitable classification or combinations thereof. Thus, the biosignal data transmitted by the plurality of electrodes 127 and received by the connection module 132 may inform device usage classifications made by AI based coaching models stored on the connection module 132 and/or any other suitable processing device (e.g., user computing devices 112c3, 112c4).

Further, as illustrated for FIG. 2A, the prosthetic device 124 may include a button 128, an indicator 129 (e.g., an LED or visual indicator), and a tactile interface 130. Generally, the button 128 may enable the user 123 to interact with the prosthetic device 124 to modify, control, and/or otherwise change the user's 123 control over the prosthetic device 124. The indicator 129 may illuminate, for example, in response to certain signals in order to notify the user 123 as to the quality of the biosignal data received by the plurality of electrodes 127. However, it should be understood that the indicator 129 may provide indications to the user 123 through an auditory stimulus, a tactile stimulus, a visual stimulus, and/or any other suitable type of stimulus. Moreover, the tactile interface 130 may enable the user 123 to interact with the connection module 132, the user computing devices 112c3, 112c4 and/or any external servers (e.g., server(s) 102) to control the calibration of the prosthetic device 124.

In particular, the communication component 132 may receive inputs from the plurality of electrodes 127 and/or the prosthetic device 124 via the button 128, and the communication component 132 may transmit some/all of those inputs to the user computing devices 112c3, 112c4 through a wireless communication component (e.g., 132c). For example, the wireless communication component 132c may utilize any suitable communication protocols/standards, such as a USB based wireless transmitter communicating via BLUETOOTH, WIFI, and/or any other radio-based communication standard.

Generally, in order to calibrate the prosthetic device 124, the user computing devices 112c3, 112c4 and/or the communication component 132 may begin or initiate a calibration procedure. The calibration procedure may generally include a specific coaching procedure identified by the devices 112c3, 112c4 and/or the communication component 132 as a result of applying user-specific biosignal data to an AI based coaching model (e.g., first AI based coaching model 114a). The model may receive the user-specific biosignal data as input, and may output a device usage classification (e.g., gesture classification, such as "pinch", "flex", etc.), which the devices 112c3, 112c4 and/or the communication component 132 may analyze to initiate the specific coaching procedure configured to improve the user's 123 control over the prosthetic device 124.

In any event, the devices 112c3, 112c4 and the communication component 132 may provide coaching instructions that guide the user 123 through a select series of motions or calibration classes, such as, e.g., an indicated motion 134, including any one or more of an elbow motion ("flex" and/or "extend"), wrist motion ("pronate" and/or "supinate"), and/or a hand motion ("open," "close," "tool," "key," and/or "pinch"), and as prompted by the calibration protocol as executed by the devices 112c3, 112c4 and the communication component 132. For example, in various embodiments, the devices 112c3, 112c4 and the communication component 132 may analyze biosignal data (e.g., EMG data) captured by the plurality of electrodes 127 that indicates a relationship between the current configuration of the prosthetic device 124 and each prompted motion (e.g., elbow motion ("flex" and/or "extend"), wrist motion ("pronate" and/or "supinate"), and/or hand motion ("open," "close," "tool," "key," and/or "pinch")) from the calibration protocol. The devices 112c3, 112c4 and the communication component 132 may then categorize the biosignal data and prepare it for viewing and/or interpretation by the user 123 to provide meaningful feedback on the quality of the calibration performed.

As part of the feedback after a calibration procedure, the devices 112c3, 112c4 and the communication component 132 may provide the user 123 with a quality metric based on the collected biosignal data. For example, the devices 112c3, 112c4 and/or the communication component 132 may include a pattern recognition component (not shown) that may be used to receive, analyze, and output biosignal data. In some embodiments, this pattern recognition component may also contain an adaptive machine learning system or model to recognize the user's 123 unique biosignal data. The adaptive machine learning system may then reference/map this user-specific biosignal data to a particular motion (e.g., a calibration class) performed by the user (e.g., any of "open," pronate," "close," and/or "supinate"). The pattern recognition component may also provide an identification to the user-specific biosignal data, and related motion (e.g., indicated motion 134), and categorize or group this information, e.g., across unique biosignal data values unique to a given user. The pattern recognition component may be coupled to a user interface (e.g., 125 or 126) for communication of the categorized user-specific biosignal data, via one or more messages, to user 123.

In various embodiments, the pattern recognition component of the devices 112c3, 112c4 and/or the communication component 132 may be configured to determine statistics from EMG biosignal data during a calibration procedure for providing recommendations to the user 123 for improved control of their prosthetic device 124. Namely, based on statistical analysis of the user's 123 EMG biosignal data, the pattern recognition component may identify common user errors (e.g., "liftoff") and suggest potential solutions to the user 123. For example, statistical values determined and analyzed by the pattern recognition component may include covariance of time domain features, signal magnitude, variation of signal magnitude over time, separation index between motion classes, frequency of electrode liftoff, and/or a variety of others statistical values or combinations thereof.

Additionally, or alternatively, the devices 112c3, 112c4 and/or the communication component 132 may apply fuzzy logic to these statistical values to indicate when a specific, but widely observed error, is likely to be occurring, e.g., as caused by user error and/or user contact with one or more of the plurality of electrodes 127. In such embodiments, the devices 112c3, 112c4 and/or the communication component 132 may apply fuzzy logic to each statistical value. Additionally, or alternatively, the devices 112c3, 112c4 and/or the communication component 132 may convert the statistical values generated from the user-specific biosignal data into values compatible with fuzzy logic by assigning a stochastic value indicating a confidence that the statistical value is outside an expected range.

Regardless, the devices 112c3, 112c4 and/or the communication component 132 may analyze these statistical values (e.g., by a pattern recognition component) for specific combinations that indicate common problems (e.g., "liftoff"). For example, such problems may include issues with signal distinctness, issues demonstrating muscle contractions during the recording, over-exertion, poor electrode 127 connection, timing issues during calibration, noise issues, signal similarity issues, and/or other issues or combinations thereof. Each issue may correspond to a calibration class, which together, or individually, the devices 112c3, 112c4 and/or the communication component 132 may assign a rating to be displayed to the user 123 as described.

Generally, the devices 112c3, 112c4 and/or the communication component 132 may analyze the severity of each common issue recognized based on the analysis of the statistical values, and may determine that a particular issue is the root cause of the user's 123 poor control over their prosthetic device 124. As a result, the devices 112c3, 112c4 and/or the communication component 132 may select one or more message types or otherwise messages to send to the user 123 to help the user 123 better understand the causes of their prosthetic device 124 control issues. These messages may include a rating (e.g., data quality metric(s)) indicating an expected performance of the prosthetic device 124 after the calibration procedure, as well as directed messages indicating what was detected during the calibration procedure, and what can be done to correct for any mistakes/errors in subsequent calibrations.

Thus, the calibration procedure initiated/conducted by the devices 112c3, 112c4 and the communication component 132 enable the user 123 to generally improve their control over the prosthetic device 124 and to receive feedback related to the calibration procedure. However, as previously mentioned, this calibration procedure can typically suffer from a lack of biosignal data for an individual user (e.g., user 123), resulting in less accurate calibrations and less accurate control over the individual user's prosthetic device (e.g., prosthetic device 124). In order to alleviate these issues, the devices 112c3, 112c4 and/or the communication component 132 may transmit the user-specific biosignal data to a server (e.g., server(s) 102), where the server aggregates such user-specific biosignal data for multiple users who are connected to a network (e.g., network 120). This server may then train an enhanced AI based coaching model (e.g., enhanced AI based coaching model 114b) and transmit the enhanced AI based coaching model to the devices 112c3, 112c4 and/or the communication component 132 to replace the first AI based coaching model (e.g., first AI based coaching model 114a). As discussed further herein in reference to FIGS. 3A-3B, this training and updating of the AI based coaching models utilized by the devices 112c3, 112c4 and/or the communication component 132 may eliminate the lack of data issues experienced by conventional calibration techniques.

FIG. 2B illustrates an alternative embodiment of the button 128 and the plurality of electrodes 127 of FIG. 2A, in accordance with various embodiments disclosed herein. The alternative embodiment illustrated in FIG. 2B also includes a connector 133 to a prosthetic device (e.g., prosthetic device 124), a button housing 131, and the connection module (e.g., connection module 132) including various hardware components 132a, 132b, and 132c. In some embodiments, the components of the button 128 may be enclosed within the button housing 131 of substantially rigid material.

In various embodiments, a myoelectric prosthetic controller, which may be configured or calibrated to control a prosthetic device (e.g., prosthetic device 124), may be included in one or both of the hardware components 132a and/or 132b. The hardware component 132c may receive inputs from one or both of the hardware components 132a, 132b through a wireless communication standard/protocol, and may transmit those inputs to a user computing device (e.g., user computing devices 112c3, 112c4) component (e.g., 132c) to which the component 132c may be communicatively coupled (e.g., inserted into a USB port). For example, the hardware component 132c may utilize any suitable communication protocols/standards, such as a USB based wireless transmitter communicating via BLUETOOTH, WIFI, and/or any other radio-based communication standard.

FIG. 3A is a block diagram representing a training sequence 300 performed by the cloud based sever 102 of FIG. 1 in order to train the enhanced AI based coaching model (e.g., enhanced AI based coaching model 114b), in accordance with various embodiments disclosed herein. Generally speaking, the training sequence 300 includes the cloud-based server 102 aggregating biosignal data from a plurality of biosignal enabled devices 302a-n with a first AI based coaching model 114a at a first time instance 304a, using the aggregate biosignal data as input to train an enhanced AI based coaching model 114b to output device usage classifications, and transmitting the enhanced AI based coaching model 114b to each of the plurality of biosignal enabled devices 302a-n at a second time instance 304b. Of course, as discussed herein, the plurality of biosignal enabled devices 302a-n may include any suitable number of devices, such that n may be any integer value. Further, the cloud based server 102 may be or include the server(s) 102 of FIG. 1.

More specifically, each biosignal enabled device 302a-n may accumulate user-specific biosignal data for the respective user of the biosignal enabled device 302a-n. For example, the biosignal enabled device 302a may accumulate user-specific biosignal data for a first user who is using the device 302a, the biosignal enabled device 302b may accumulate user-specific biosignal data for a second user who is using the device 302b, the biosignal enabled device 302c may accumulate user-specific biosignal data for a third user who is using the device 302c, and so forth. Each of the biosignal enabled devices 302a-n may accumulate this user-specific biosignal data at any suitable time during operation of the user's prosthetic device, and in particular, during a calibration procedure conducted by a user with their respective device 302a-n and the first AI based coaching model 114a. When any of the biosignal enabled devices 302a-n accumulates user-specific biosignal data corresponding to the respective user, the device 302a-n may transmit the user-specific biosignal data to the cloud based server 102.

The cloud based server 102 may aggregate this user-specific biosignal data from the various biosignal enabled devices 302a-n until the server 102 determines that a sufficient amount of data has been aggregated to validate training an enhanced AI based coaching model 114b. Of course, the sufficient amount of data may constitute any suitable amount of data, such as user-specific biosignal data from a single biosignal enabled device 302a-n. In any event, when the cloud based server 102 determines that such a sufficient amount of data has been obtained from the one or more of the biosignal enabled devices 302a-n, the cloud based server 102 may begin training the enhanced AI based coaching model 114b with the aggregated biosignal data input as training data. In particular, the cloud based server 102 may train the enhanced AI based coaching model 114b to output one or more device usage classifications based on the input aggregate biosignal data. In some embodiments, the aggregated biosignal data and/or any other user-specific biosignal data of one or more users may be stored in the server memory 106 and/or any respective device memory (e.g., device memory 316 of FIG. 3B) as a user profile 306 of the user.

As previously described, the user-specific biosignal data captured by the biosignal enabled devices 302a-n may include any suitable data, such as EMG data, IMU data, or the like for calibration/configuration purposes. In certain embodiments, the data collected and transmitted to the cloud based server 102 for training the enhanced AI based coaching model 114b may also include logs corresponding to time periods preceding a calibration event/procedure. In these embodiments, the cloud based server 102 may analyze this data to determine causal events leading to the calibration event/procedure. For example, electrode lead-off events may be high in the time period leading up to a calibration event/procedure. If the cloud based server determines that this is a sustained pattern across multiple calibration events/procedures, then a clinician (e.g., a prosthetist) can be notified, and in the interim, the cloud based server 102 may train the enhanced AI based coaching model 114*b* to incorporate/accommodate some degree of electrode liftoff. Moreover, the biosignal enabled device 302*a-n* and/or the cloud based server 102 may prompt a user to choose to have their data, their performance trajectory, their general quality of control, etc. stored in the server memory 106 (e.g., as part of a user profile 306) and compared against different subsets of similar users who also have user profiles 306 stored in the server memory 106. For example, the criteria for determining similar subsets of users may include any single, or combination of: age, amputation level, amputation cause, gender, and/or any other suitable criteria or combinations thereof.

More generally, the cloud based server 102 may train the enhanced AI based coaching model 114*b* using a supervised machine learning program or algorithm, such as a multivariate regression analysis or neural network. Machine learning may involve identifying and recognizing patterns in existing data (such as generating device usage classifications corresponding to the user-specific biosignal data of respective individuals) in order to facilitate making predictions or identification for subsequent data (such as using the model on new user-specific biosignal data in order to determine or generate a device usage classification corresponding to the new user-specific biosignal data of a user). Machine learning model(s), such as the enhanced AI based coaching model 114*b* described herein for some aspects, may be created and trained based upon example data (e.g., "training data" and related user-specific biosignal data) inputs or data (which may be termed "features" and "labels") in order to make valid and reliable predictions for new inputs, such as testing level or production level data or inputs.

In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, patterns, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based on the discovered rules, relationships, or model, an expected output.

As an example, the cloud based server 102 may train the enhanced AI based coaching model 114*b* using a gradient decent algorithm. Such gradient descent algorithms may be used in machine learning to find values of a function's parameters (coefficients) that minimize a corresponding cost or error function. By minimizing (or in some cases, eliminating) the cost/error, the resulting enhanced AI based coaching model 114*b* is improved, for example, by providing more accurate device usage classifications, and thereby enabling improved operation of the underlying biosignal enabled device 302*a-n*. In particular, the cloud based server 102 may perform the gradient descent algorithm to train the enhanced AI based coaching model 114*b* by identifying a local minimum of a differentiable function, wherein the local minimum defines a lowest error value and/or a lowest cost/error function that may correspond to, for example, the device usage classification error rate of the model 114*b*.

Further, in certain embodiments, the server processor 104 may execute the enhanced AI based coaching model 114*b* to detect one or more errors, such as to determine whether or not the device classification error rate is sufficiently minimized to conclude training the model 114*b*. In these embodiments, the one or more errors may comprise, for example: (1) when an output device usage classification fails to match an expected device usage classification selected from the one or more device usage classifications; or (2) when an output device usage classification fails to fall within one or more predetermined threshold values. In this manner, the server processor 104 may identify whether or not the enhanced AI based coaching model 114*b* is sufficiently trained for deployment to the various connected biosignal enabled devices 302*a-n* based on how frequently and/or how erroneously/egregiously the model 114*b* misclassifies the usage of a particular device.

In certain aspects, the enhanced AI based coaching model 114*b* may be trained using multiple supervised machine learning techniques, and may additionally or alternatively be trained using one or more unsupervised machine learning techniques. In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated.

For example, in certain aspects, the enhanced AI coaching model 114*b* may employ a neural network, which may be a convolutional neural network, a deep learning neural network, or a combined learning module or program that learns in two or more features or feature datasets (e.g., user-specific data) in particular areas of interest. The machine learning programs or algorithms may also include natural language processing, semantic analysis, automatic reasoning, support vector machine (SVM) analysis, decision tree analysis, random forest analysis, K-Nearest neighbor analysis, naïve Bayes analysis, clustering, reinforcement learning, and/or other machine learning algorithms and/or techniques. In some aspects, the artificial intelligence and/or machine learning based algorithms may be included as a library or package executed on the server(s) 102. For example, libraries may include the TENSORFLOW based library, the PYTORCH library, and/or the SCIKIT-LEARN Python library.

Regardless, training the enhanced AI based coaching model 114*b* may also comprise retraining, relearning, or otherwise updating models with new, or different, information, which may include information received, ingested, generated, or otherwise used over time.

When the cloud based server 102 determines that the enhanced AI based coaching model 114*b* is adequately trained, the server 102 may provide the enhanced AI based coaching model 114*b* to the biosignal enabled devices 302*a-n*. The server 102 may transmit the enhanced AI based coaching model 114*b* across a network (e.g., network 120) via the networking interface 308 to each of the biosignal enabled devices 302*a-n* for download and implementation. Each biosignal enabled device 302*a-n* may receive the enhanced AI based coaching model 114*b*, and may replace or update the first AI based coaching model 114*a* in the device memory, such that the devices 302*a-n* may only apply the enhanced AI based coaching model 114*b* to any subsequently received user-specific biosignal data to generate device usage classifications.

FIG. 3B is a block diagram representing data input and output to/from a biosignal enabled device of FIGS. 1, 2A, and 3A, including the enhanced AI based coaching model 114*b* of FIG. 3A, to initiate a coaching procedure for a user, and in accordance with various embodiments disclosed herein. As illustrated in FIG. 3B, the biosignal enabled device 312 may receive the enhanced AI coaching model at a first time instance 311*a*. The device 312 may receive the enhanced AI coaching model from a cloud based server (e.g., cloud based sever 102) across a network (e.g., network 120) via the networking interface 320. At this first time instance 311*a*, the biosignal enabled device 312 may have a first AI based coaching model 114*a* stored in device memory 316. When the biosignal enabled device 312 receives the enhanced AI coaching model, the device processor 314 may automatically replace and/or update the first AI based coaching model 114*a* with the enhanced AI based coaching model. Additionally, or alternatively, when the biosignal enabled device 312 detects the enhanced AI based coaching model, the device 312 may generate a notification to the user (e.g., user 123) notifying them that the enhanced AI based coaching model is available for execution on the device 312.

Thus, at a second time instance 311*b*, the biosignal enabled device 312 may receive user-specific biosignal data, and may proceed to apply the enhanced AI coaching model 114*b* to the user-specific biosignal data instead of the first AI based coaching model 114*a*. In particular, the biosignal enabled device 312 may receive user-specific biosignal data, and may apply the enhanced AI based coaching model 114*b* to the user-specific biosignal data to output a device usage classification. The device processor 314 may analyze the device usage classification output by the enhanced AI based coaching model 114*b* to determine and initiate a coaching procedure based on the device usage classification. The coaching procedure may generally cause the device processor 314 and/or another suitable processor (e.g., processors of user computing devices 112*c*3, 112*c*4) to render visual instructions on a display screen communicatively coupled to the biosignal enabled device 312. The coaching procedure may include visual instructions in order to coach the user how to use and/or configure the biosignal enabled device 312 to implement an updated configuration for the biosignal enabled device 312.

Moreover, the biosignal enabled device 312 may store some/all of the user-specific biosignal data as part of a user profile 318 corresponding to the user. In certain embodiments, the biosignal enabled device 312 may also transmit this user profile 318 to a cloud based server (e.g., cloud based server 102) for storage as part of an aggregated set of user profiles (e.g., user profiles 306).

FIG. 3C is a block diagram representing data input and output to/from a biosignal enabled device 322 of FIGS. 1, 2A, and 3A to modify an operation configuration of the biosignal enabled device 322, in accordance with various embodiments disclosed herein. In general, the configuration of the biosignal enabled device 322 may reference various settings/operating parameters of the biosignal enabled device 322 that cause the device 322 to control and/or otherwise communicate with a user's prosthetic device. However, it should be understood that the configuration updates provided herein may also reference settings/operating parameters of a user's prosthetic device, electrodes (e.g., plurality of electrodes 127) connecting the user's appendage to the device 322 and prosthetic device, and/or any other suitable device that is communicatively coupled to the biosignal enabled device 322.

For example, the biosignal enabled device 322 may utilize multiple communication channels when transmitting control instructions and/or other communications to the prosthetic device or to any other communicatively coupled device (e.g., user computing devices 112*c*3, 112*c*4, cloud based server 102). A variety of circumstances may lead to one or more of these communication channels being inoperative, malfunctioning, and/or otherwise undesirable for the biosignal enabled device 322 to use when transmitting signals. By contrast, circumstances may arise that the biosignal enabled device 322 would benefit from utilizing additional/different communication channels when transmitting different signals. In any event, if it is clear that the communication channel setting(s) of the biosignal enabled device 322 should be changed to enhance performance of the device 322, then the device 322 may receive a suitable configuration update to make the necessary communication channel setting changes from the user 123, the cloud based server 102, and/or a medical professional 321.

Of course, the configuration update may be provided by the user 123, the medical professional 321, and/or the cloud based server 102 in order to adjust any suitable settings/operating parameters of the biosignal enabled device 322. Continuing the above example, the user 123 may input the configuration update by, for example, manually turning one or more communication channels of the device 322 on/off. The device 322 may also receive a configuration update from the cloud based server 102 causing the biosignal enabled device 322 to automatically adjust one or more communication channels on/off via the device processor 324. Further, the medical professional 321 may have access to the biosignal enabled device 322 via a specialist portal (e.g., specialist portal GUI 400, 410 of FIGS. 4A and 4B) communicated over a network (e.g. network 120) via the networking interface 330, and may remotely transmit the configuration update to the biosignal enabled device 322 in order to adjust one or more communication channels on/off via the device processor 324.

In certain embodiments, the configuration update may be stored and/or otherwise modify/adjust settings of the biosignal enabled device 322 or other suitable device, as identified in the user profile 328 stored in the device memory 326. The user profile 328 may receive the configuration update which may cause the biosignal enabled device 322 to operate according to an improved operation configuration, as identified in the configuration update. In these embodiments, the configuration update may be provided by at least one of: (i) modification of configuration settings, by the user 123 or the medical professional 321, of the biosignal enabled device 322; or (ii) modification of configuration settings, as automatically downloaded or transmitted from the cloud based server 102 to the biosignal enabled device 322, for implementation by the biosignal enabled device 322.

FIG. 4A illustrates an example specialist portal graphical user interface (GUI) 400 rendered on a display screen 401 of a computing device 112*c*3 communicatively coupled to the cloud based server (e.g., cloud based server 102), the example specialist GUI 400 being configured to provide access to a medical professional to read, modify, or provide coaching instructions to the user, and in accordance with various embodiments disclosed herein. In general, the specialist GUI 400 may allow a clinician to view all of the user-specific biosignal data collected by a user's biosignal enabled device in order to help the user better control their prosthetic device. The specialist GUI 400 includes a clinician view panel 402*a*, a data review panel 402*b*, and a device select panel 402*c*.

The clinician view panel 402a enables the user to view the clinician, and the clinician to optionally view the user (e.g., via an integrated and/or separate camera coupled to the user computing device 112c3). The data review panel 402b may generally show results and user-specific biosignal data corresponding to a recent calibration event/procedure and/or overall/historical user-specific biosignal data for the user. The device select panel 402c may enable the user to switch between user-specific biosignal data acquired for the user's real prosthetic device and/or a user's virtual arm, may enable the user to enter a VR space to play games/activities with the clinician, and/or may enable the clinician to make configuration adjustments/modifications to the settings or other operational parameters of the user's virtual arm or prosthetic device. Of course, these descriptions of the various panels 402a, 402b, and/or 402c are for the purposes of discussion only, and additional functionalities are contemplated for each panel 402a, 402b, 402c. For example, the specialist GUI 400 may enable the clinician to view the EMG signals, adjust settings, push control coach messages, turn on/off communication channels, and/or other suitable actions or combinations thereof using any of the panels 402a, 402b, 402c.

Further, the specialist GUI 400 enables a user to receive virtual doctor visits with the clinician. During these virtual visits through the specialist GUI 400, the user may, for example, be in virtual reality (VR) with their prosthetic device, and the user may engage in an appointment with their clinician. The clinician may view and/or otherwise observe the user's prosthetic device in real time, and may help the user learn how to use the prosthetic device. Additionally, during such visits and/or otherwise appointments through the specialist GUI 400, the user may engage in virtual games/activities between the user and clinician to further assist the user in learning how to control their prosthetic device, and the clinician may actively monitor/review the data resulting from these games/activities.

In any event, the specialist GUI 400 may be implemented or rendered via an application (app) executing on user computing device 112c3. For example, the specialist GUI 400 may be implemented or rendered via a native app executing on the user computing device 112c3. In the example of FIG. 4A, the user computing device 112c3 is a user computing device as described for FIG. 1, e.g., where 112c3 is illustrated as an APPLE iPhone that implements the APPLE iOS operating system and that has display screen 401. The user computing device 112c3 may execute one or more native applications (apps) on its operating system, including, for example, the diagnostic app, as described herein. Such native apps may be implemented or coded (e.g., as computing instructions) in a computing language (e.g., SWIFT) executable by the user computing device operating system (e.g., APPLE iOS) by the processor of user computing device 112c3.

Additionally, or alternatively, specialist GUI 400 may be implemented or rendered via a web interface, such as via a web browser application, e.g., Safari and/or Google Chrome app(s), or other such web browser or the like. More specifically, the specialist portal (as embodied by the specialist GUI 400) may be rendered via such websites or web browser applications hosted by the cloud based server (e.g., cloud based server 102) and/or a mobile application in communication with the cloud based server 102. For example, the user computing device 112c3 may receive instructions from a cloud based server (e.g., cloud based server 102) to render, on the display screen 401, the specialist GUI 400 in order to provide access to a medical professional to read, modify, or provide coaching instructions to the user via the display screen through any of panels 402a, 402b, 402c. In certain embodiments, the specialist GUI 400 may include one or more options to adjust or configure operation of the biosignal enabled device of the user, such as through panels 402b, 402c.

As previously mentioned, the specialist GUI 400 may be configured to launch a virtual meeting between the medical professional and the user. In such a virtual meeting the display screen may provide/display: (i) virtual instructions regarding set-up of the biosignal enabled device; (ii) the user-specific biosignal data of the user as collected by the biosignal enabled device; (iii) a comparison of the user-specific biosignal data of the user to a second set of biosignal data of at least one additional user; (iv) modulations to one or more settings of the biosignal enabled device of the user; (v) one or more suggestions for improving a performance of the biosignal enabled device of the user; and/or (vi) training to improve a performance of the biosignal enabled device of the user. It should be understood that any/all of these actions enabled by the virtual meeting, such as modulating the settings of the biosignal enabled device, may be performed by the medical professional and/or the user during the virtual meeting.

In addition, the user may select the data review panel 402b (or any suitable panel 402a, 402c) to recalibrate the user's biosignal enabled device based on new user-specific biosignal data. Selecting and/or otherwise interacting with the data review panel 402b may cause the specialist GUI 400 to prompt the user to perform (optionally under the supervision of the clinician via the panel 402a) a calibration procedure in order to receive an up-to-date calibration analysis for display in the specialist GUI 400. The enhanced AI based coaching model (e.g., enhanced AI based coaching model 114b), executing on the memory of the biosignal enabled device (e.g., biosignal enabled device 322), may analyze the new user-specific biosignal data to generate a new device usage classification. The biosignal enabled device may then determine and initiate a new coaching procedure based on this new device usage classification. The clinician may view the results of the recent calibration, and may comment and/or otherwise interact with the user during the new coaching procedure to ensure that the user receives a maximal benefit from the coaching procedure. The calibration results and/or results of the coaching procedure may also appear in the data review panel 402b during and/or after the calibration and/or the coaching procedure.

In various aspects, the new user-specific biosignal data, the new device usage classification, the new coaching procedure, and/or any data associated therewith may be transmitted via a computer network, from the biosignal enabled device and/or a communicatively coupled user computing device 112c3 to a cloud based server (e.g., cloud based server 102) for training of a new enhanced AI based coaching model and/or to update the user's respective user profile (e.g., user profiles 306) stored in the server memory (e.g., server memory 106).

FIG. 4B illustrates another example specialist GUI 410 rendered on a display screen 411 of another user computing device 112c4 communicatively coupled to the biosignal enabled device (e.g., biosignal enabled device 322), in accordance with various embodiments disclosed herein. Generally speaking, the example specialist GUI 410 is similar to the specialist GUI 400 of FIG. 4A, in that similar functionality is possible with the specialist GUI 410 that was also possible with specialist GUI 400. However, the specialist GUI 410 highlights other panels that may be displayed as part of a GUI rendered by the cloud based server (e.g., cloud based server 102), user computing device 112c4, and/or the biosignal enabled device for a user to interact with a clinician.

Namely, the specialist GUI 410 includes a clinician view panel 412a, a first user-specific biosignal data review panel 412b, and a second user-specific biosignal data review panel 412c. The clinician view panel 412a enables the user to view the clinician, and the clinician to optionally view the user (e.g., via an integrated and/or separate camera coupled to the user computing device 112c4). The first user-specific biosignal data review panel 412b and the second user-specific biosignal data review panel 412c may generally show results and user-specific biosignal data corresponding to a recent calibration event/procedure and/or overall/historical user-specific biosignal data for the user. In particular, the first user-specific biosignal data review panel 412b may show various groupings and corresponding categorizations of EMG signal data acquired in response to a user performing specified motions as part of a calibration procedure (e.g., any of "open," pronate," "close," "supinate," etc. as shown in panel 412b). The second user-specific biosignal data review panel 412c may show time-dependent representations of EMG signal data received by the biosignal enabled device during calibration by the user.

Moreover, in certain embodiments, the specialist GUI 410 may include additional biosignal data that is collected from other users. For example, the second user-specific biosignal data review panel 412c may include a first EMG signal graph that is representative of EMG signal data from a recent calibration event/procedure and/or overall/historical user-specific biosignal data for the user, and the panel 412c may also include a second EMG signal graph that is representative of EMG signal data from a recent calibration event/procedure and/or overall/historical user-specific biosignal data for a different user. Thus, the biosignal enabled device may cause the user computing device to graphically render the user-specific biosignal data of the user, as collected by the biosignal enabled device, with a second set of biosignal data as collected from at least one additional user (e.g., the different user in the previous example).

Of course, these descriptions of the various panels 412a, 412b, 412c are for the purposes of discussion only, and additional functionalities are contemplated for each panel 412a, 412b, 412c. For example, the specialist GUI 410 may enable the clinician to view the EMG signals, adjust settings, push control coach messages, turn on/off communication channels, and/or other suitable actions or combinations thereof using any of the panels 412a, 412b, 412c.

FIG. 4C illustrates an example GUI 420 configured to display performance metrics indicating performance improvement (e.g., performance improvement section 422b1) of a user's biosignal enabled device as a result of coaching the user to configure the biosignal enabled device based on the device classification output by the enhanced AI based coaching model of FIGS. 1 and 3A-3C, and in accordance with various embodiments disclosed herein. In general, the example GUI 420 includes multiple graphical/textual renderings that present data and/or results to a user associated with a calibration procedure of the user's biosignal enabled device. More specifically, the example GUI 420 includes a data summary panel 422a, and a data description panel 422b, which includes the performance improvement section 422b1. Broadly, the data summary panel 422a may display general results of the user's calibration procedure of the biosignal enabled device based on the user-specific biosignal data corresponding to various components and/or motions of the prosthetic device. Similarly, the data description panel 422b may display more specific results of the user's calibration procedure of the biosignal enabled device, and in particular, may display textual renderings indicating performance improvement techniques/suggestions/tips, as well as the performance improvement section 422bl.

The performance improvement section 422b1 may include a performance metric (e.g., 11%) indicating a performance improvement of the biosignal enabled device of the user as a result of a calibration procedure and/or a coaching procedure performed by the user. Thus, as illustrated in FIG. 4C, the performance improvement section 422b1 indicates to the user that their performance during a calibration procedure and/or a coaching procedure corresponding to the user's biosignal enabled device and prosthetic device improved by 11% relative to a prior performance, a historical performance average, etc. of the calibration procedure and/or coaching procedure. In certain embodiments, the performance metric may be stored in the device memory of the biosignal enabled device and/or in the server memory of the cloud based server.

Additionally, the textual renderings and graphical renderings in the data summary panel 422a and the data description panel 422b may show user-specific results (e.g., 1-5 stars corresponding to motions of the elbow, wrist, hand, etc.) which may indicate that the user has a low/high degree of control over the prosthetic device as a result of the calibration performed for the biosignal enabled device. The 5 stars graphical rendering in the data summary panel 422a may indicate that the user has a relatively high degree of control as a result of the calibration and/or coaching procedure, such that the user may not require additional and/or different coaching and/or calibration to improve the user's control of the prosthetic device using the biosignal enabled device. By contrast, the 3 stars graphical rendering in the data summary panel 422a corresponding to the user opening the hand of the prosthetic device may indicate that the user has a relatively average degree of control as a result of the calibration and/or coaching procedure, such that the user may benefit from additional and/or different coaching and/or calibration specifically designed to improve the user's control of the hand of the prosthetic device (e.g., increase the ability of the user to open the hand of the prosthetic device).

It is to be understood that other graphical rendering and/or textual rendering types or values are contemplated herein, where additional graphical rendering and/or textual rendering types or values may be rendered to represent and/or otherwise indicate, for example, a performance improvement metric or the like. Additionally, or alternatively, color values may be used and/or overlaid on a graphical rendering (e.g., graphical renderings of the user's ratings in the data summary panel 422a) shown on example GUI 420 to indicate a degree or quality of a given score, e.g., a 3 star rating or a 5 star rating.

In various embodiments, any of the graphical renderings and/or textual renderings in the example GUI 420 may be transmitted, via the computer network (e.g., from the cloud based server 102 and/or one or more processors) to the user computing device 112c3, for rendering on the display screen 421. In other aspects, each of the graphical renderings and/or textual renderings included in the example GUI 420 may instead be generated locally, by the user's computing device (e.g., user computing device 112c3) and rendered, by a device processor of the mobile device, on display screen 412 of the mobile device (e.g., user computing device 112c3).

Further, in some embodiments, any of the graphical renderings and/or textual renderings in the example GUI 420 may be rendered (e.g., rendered locally on display screen 412) in real-time or near-real time during or after receiving, the user-specific biosignal data and/or any analyzed results of a calibration procedure and/or a coaching procedure.

FIG. 5 is a block diagram flowchart representing an example cloud-enabled and AI based biosignal method 500 for enhancing biosignal enabled devices based on device usage, in accordance with various embodiments disclosed herein. At block 502, the method 500 comprises aggregating, at a cloud based server (e.g., cloud based server 102) comprising a server processor (e.g., server processor 104) and a server memory (e.g., server memory 106), biosignal data as collected from respective users of one or more biosignal enabled devices. Each of the one or more biosignal enabled devices (e.g., biosignal enabled devices 302*a-n*) may comprise a device processor (e.g., device processor 324) and a device memory (e.g., device memory 326) storing a first AI based coaching model (e.g., first AI based coaching model 114*a*), and each of the one or more biosignal enabled devices may be configured to collect biosignal data from the respective users.

The method 500 may further include training an enhanced AI based coaching model with the aggregated biosignal data as input as training data (block 504). The enhanced AI based coaching model may be configured to output one or more device usage classifications. In certain embodiments, the server computing instructions, when executed by the server processor, may cause the server processor to: execute the enhanced AI based coaching model to detect one or more errors. In particular, the one or more errors may comprise one or more of: (1) when an output device usage classification fails to match an expected device usage classification selected from the one or more device usage classifications; or (2) when an output device usage classification fails to fall within one or more predetermined threshold values.

The method 500 may further include providing the enhanced AI based coaching model to the one or more biosignal enabled devices (block 506). The enhanced AI based coaching model may replace and/or update the first AI based coaching model in the device memory of the one or more biosignal enabled devices. In certain embodiments, at least one of the one or more biosignal enabled devices comprises a wearable device. In some embodiments, the respective device processor comprises one or more of: a local processor coupled with the biosignal enabled device; or a remote processor wirelessly connected to a computing device.

The method 500 may further include receiving, at a biosignal enabled device of a user, user-specific biosignal data of the user (block 508). The biosignal enabled device of the user may comprise one of the one or more biosignal enabled devices. In certain embodiments, the user-specific biosignal data of the user is stored in the respective device memory or the server memory as a user profile of the user. In these embodiments, the user profile may receive a configuration update causing the biosignal enabled device to operate according to an improved operation configuration. This configuration update may be provided by at least one of: modification of configuration settings, by the user or a medical professional, of the biosignal enabled device; or modification of configuration settings, as automatically downloaded or transmitted from the cloud based server to the biosignal enabled device, for implementation by the biosignal enabled device.

The method 500 may further include inputting, at the biosignal enabled device of the user, the user-specific biosignal data into the enhanced AI based coaching model (block 510). The enhanced AI based coaching model may output a device usage classification. In certain embodiments, the biosignal enabled device of the user may comprise a controller configured to control a prosthetic device. In these embodiments, the device computing instructions, when executed by the respective device processor, may cause the respective device processor to: calibrate the controller to control the prosthetic device based on the user-specific biosignal data of the user.

The method 500 may further include initiating a coaching procedure based on the device usage classification (block 512). The coaching procedure may cause rendering of visual instructions on a display screen communicatively coupled to the biosignal enabled device of the user. The visual instructions may be provided to coach the user how to use or configure the biosignal enabled device of the user to implement an updated configuration for the biosignal enabled device of the user. In certain embodiments, a performance metric indicating a performance improvement of the biosignal enabled device of the user may be stored in the respective device memory of the biosignal enabled device of the user or the cloud based server. Further in these embodiments, the performance metric may be rendered on the display screen.

In some embodiments, the device computing instructions, when executed by the respective device processor, may further cause the respective device processor to: graphically render the user-specific biosignal data of the user, as collected by the biosignal enabled device, with a second set of biosignal data as collected from at least one additional user.

In certain embodiments, the server computing instructions, when executed by the server processor, may further cause the server processor to: render, on a display screen of a computing device communicatively coupled to the cloud based server, a specialist portal comprising a specialist graphical user interface (GUI) configured to provide access to a medical professional to read, modify, or provide coaching instructions to the user via the display screen. In these embodiments, the specialist GUI may comprise one or more options to adjust or configure operation of the biosignal enabled device of the user. Further, the specialist GUI may be configured to launch a virtual meeting between the medical professional and the user. Such a virtual meeting may comprise at least one of: providing, via the display screen, virtual instructions regarding set-up of the biosignal enabled device; providing, via the display screen, the user-specific biosignal data of the user as collected by the biosignal enabled device; providing, via the display screen, a comparison of the user-specific biosignal data of the user to a second set of biosignal data of at least one additional user; modulating, by the respective device processor, one or more settings of the biosignal enabled device of the user; providing, via the display screen, one or more suggestions for improving a performance of the biosignal enabled device of the user; and/or training, via the display screen, the user to improve a performance of the biosignal enabled device of the user.

Aspects of the Disclosure

1. A cloud-enabled and artificial intelligence (AI) based biosignal system configured to enhance biosignal enabled devices based on device usage, the cloud-enabled and artificial intelligence biosignal system comprising: one or more biosignal enabled devices, each of the one or more biosignal enabled devices comprising a device processor and a device memory storing a first AI based coaching model, and each of the one or more biosignal enabled devices configured to collect biosignal data from respective users; server computing instructions configured for execution on a cloud based server comprising a server processor and a server memory, wherein the cloud based server is communicatively coupled to the one or more biosignal enabled devices, wherein the server computing instructions, when executed by the server processor, cause the server processor to: aggregate biosignal data as collected from respective users of the one or more biosignal enabled devices, train an enhanced AI based coaching model with the aggregated biosignal data as input as training data, wherein the enhanced AI based coaching model is configured to output one or more device usage classifications, and provide the enhanced AI based coaching model to the one or more biosignal enabled devices, wherein the enhanced AI based coaching model replaces or updates the first AI based coaching model in the device memory of the one or more biosignal enabled devices; and device computing instructions configured for execution by a respective device processor communicatively coupled to a biosignal enabled device of a user, the biosignal enabled device of the user comprising one of the one or more biosignal enabled devices, and wherein the device computing instructions as stored in a respective device memory of the biosignal enabled device of the user, when executed by the respective device processor, causes the respective device processor to: receive user-specific biosignal data of the user, input the user-specific biosignal data into the enhanced AI based coaching model, wherein the enhanced AI based coaching model outputs a device usage classification, and initiate a coaching procedure based on the device usage classification, wherein the coaching procedure causes rendering of visual instructions on a display screen communicatively coupled to the biosignal enabled device of the user, wherein the visual instructions are provided to coach the user how to use or configure the biosignal enabled device of the user to implement an updated configuration for the biosignal enabled device of the user.

2. The cloud-enabled and AI based biosignal system of aspect 1, wherein the server computing instructions, when executed by the server processor, cause the server processor to: execute the enhanced AI based coaching model to detect one or more errors, wherein the one or more errors comprise one or more of: (1) when an output device usage classification fails to match an expected device usage classification selected from the one or more device usage classifications; or (2) when an output device usage classification fails to fall within one or more predetermined threshold values.

3. The cloud-enabled and AI based biosignal system of any of aspects 1-2, wherein the biosignal enabled device of the user comprises a controller configured to control a prosthetic device, and wherein the device computing instructions, when executed by the respective device processor, further cause the respective device processor to: calibrate the controller to control the prosthetic device based on the user-specific biosignal data of the user.

4. The cloud-enabled and AI based biosignal system of any of aspects 1-3, wherein a performance metric indicating a performance improvement of the biosignal enabled device of the user is stored in the respective device memory of the biosignal enabled device of the user or the cloud based server.

5. The cloud-enabled and AI based biosignal system of aspect 4, wherein the performance metric is rendered on the display screen.

6. The cloud-enabled and AI based biosignal system of any of aspects 1-5, wherein at least one of the one or more biosignal enabled devices comprises a wearable device.

7. The cloud-enabled and AI based biosignal system of any of aspects 1-6, wherein the device computing instructions, when executed by the respective device processor, further cause the respective device processor to: graphically render the user-specific biosignal data of the user, as collected by the biosignal enabled device, with a second set of biosignal data as collected from at least one additional user.

8. The cloud-enabled and AI based biosignal system of any of aspects 1-7, wherein the server computing instructions, when executed by the server processor, further cause the server processor to: render, on a display screen of a computing device communicatively coupled to the cloud based server, a specialist portal comprising a specialist graphical user interface (GUI) configured to provide access to a medical professional to read, modify, or provide coaching instructions to the user via the display screen.

9. The cloud-enabled and AI based biosignal system of aspect 8, wherein the specialist GUI comprises one or more options to adjust or configure operation of the biosignal enabled device of the user.

10. The cloud-enabled and AI based biosignal system of any of aspects 1-9, wherein the respective device processor comprises one or more of: a local processor coupled with the biosignal enabled device; or a remote processor wirelessly connected to a computing device.

11. The cloud-enabled and AI based biosignal system of aspect 9, wherein the specialist GUI is configured to launch a virtual meeting between the medical professional and the user.

12. The cloud-enabled and AI based biosignal system of aspect 11, wherein the virtual meeting comprises at least one of: providing, via the display screen, virtual instructions regarding set-up of the biosignal enabled device; providing, via the display screen, the user-specific biosignal data of the user as collected by the biosignal enabled device; providing, via the display screen, a comparison of the user-specific biosignal data of the user to a second set of biosignal data of at least one additional user; modulating, by the respective device processor, one or more settings of the biosignal enabled device of the user; providing, via the display screen, one or more suggestions for improving a performance of the biosignal enabled device of the user; or training, via the display screen, the user to improve a performance of the biosignal enabled device of the user.

13. The cloud-enabled and AI based biosignal system of any of aspects 1-12, wherein the user-specific biosignal data of the user is stored in the respective device memory or the server memory as a user profile of the user.

14. The cloud-enabled and AI based biosignal system of aspect 13, wherein the user profile receives a configuration update causing the biosignal enabled device to operate according to an improved operation configuration, and where the configuration update is provided by at least one of: modification of configuration settings, by the user or a medical professional, of the biosignal enabled device; or modification of configuration settings, as automatically downloaded or transmitted from the cloud based server to the biosignal enabled device, for implementation by the biosignal enabled device.

15. A cloud-enabled and artificial intelligence (AI) based biosignal method for enhancing biosignal enabled devices based on device usage, the cloud-enabled and artificial intelligence biosignal method comprising: aggregating, at a cloud based server comprising a server processor and a server memory, biosignal data as collected from respective users of one or more biosignal enabled devices, each of the one or more biosignal enabled devices comprising a device processor and a device memory storing a first AI based coaching model, and each of the one or more biosignal enabled devices configured to collect biosignal data from the respective users; training an enhanced AI based coaching model with the aggregated biosignal data as input as training data, wherein the enhanced AI based coaching model is configured to output one or more device usage classifications; providing the enhanced AI based coaching model to the one or more biosignal enabled devices, wherein the enhanced AI based coaching model replaces or updates the first AI based coaching model in the device memory of the one or more biosignal enabled devices; receiving, at a biosignal enabled device of a user, user-specific biosignal data of the user, wherein the biosignal enabled device of the user comprises one of the one or more biosignal enabled devices; inputting, at the biosignal enabled device of the user, the user-specific biosignal data into the enhanced AI based coaching model, wherein the enhanced AI based coaching model outputs a device usage classification; and initiating a coaching procedure based on the device usage classification, wherein the coaching procedure causes rendering of visual instructions on a display screen communicatively coupled to the biosignal enabled device of the user, wherein the visual instructions are provided to coach the user how to use or configure the biosignal enabled device of the user to implement an updated configuration for the biosignal enabled device of the user.

16. The cloud-enabled and AI based biosignal method of aspect 15, further comprising: executing the enhanced AI based coaching model to detect one or more errors, wherein the one or more errors comprise one or more of: (1) when an output device usage classification fails to match an expected device usage classification selected from the one or more device usage classifications; or (2) when an output device usage classification fails to fall within one or more predetermined threshold values.

17. The cloud-enabled and AI based biosignal method of any of aspects 15-16, wherein the biosignal enabled device of the user comprises a controller configured to control a prosthetic device, and wherein the method further comprises: calibrating the controller to control the prosthetic device based on the user-specific biosignal data of the user.

18. The cloud-enabled and AI based biosignal method of any of aspects 15-17, further comprising: rendering, on a display screen of a computing device communicatively coupled to the cloud based server, a specialist portal comprising a specialist graphical user interface (GUI) configured to provide access to a medical professional to read, modify, or provide coaching instructions to the user via the display screen.

19. A tangible, non-transitory computer-readable medium storing instructions for enhancing biosignal enabled devices based on device usage, that when executed by one or more processors cause the one or more processors to: aggregate, at a cloud based server comprising a server processor and a server memory, biosignal data as collected from respective users of one or more biosignal enabled devices, each of the one or more biosignal enabled devices comprising a device processor and a device memory storing a first AI based coaching model, and each of the biosignal enabled devices configured to collect biosignal data from the respective users; train an enhanced AI based coaching model with the aggregated biosignal data as input as training data, wherein the enhanced AI based coaching model is configured to output one or more device usage classifications; provide the enhanced AI based coaching model to the one or more biosignal enabled devices, wherein the enhanced AI based coaching model replaces or updates the first AI based coaching model in the device memory of the one or more biosignal enabled devices; receive, at a biosignal enabled device of a user, user-specific biosignal data of the user, wherein the biosignal enabled device of the user comprises one of the one or more biosignal enabled devices; input, at the biosignal enabled device of the user, the user-specific biosignal data to the enhanced AI based coaching model, wherein the enhanced AI based coaching model outputs a device usage classification; and initiate a coaching procedure based on the device usage classification, wherein the coaching procedure causes rendering of visual instructions on a display screen communicatively coupled to the biosignal enabled device of the user, wherein the visual instructions are provided to coach the user how to use or configure the biosignal enabled device of the user to implement an updated configuration for the biosignal enabled device of the user.

20. The tangible, non-transitory computer-readable medium of aspect 19, wherein the instructions, when executed by one or more processors, further cause the one or more processors to: execute the enhanced AI based coaching model to detect one or more errors, wherein the one or more errors comprise one or more of: (1) when an output device usage classification fails to match an expected device usage classification selected from the one or more device usage classifications; or (2) when an output device usage classification fails to fall within one or more predetermined threshold values.

The foregoing additional aspects of the disclosure are exemplary only and not intended to limit the scope of the disclosure.

Additional Considerations

Although the disclosure herein sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" or "hardware component" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed is:

1. A cloud-enabled and artificial intelligence (AI) based biosignal system configured to enhance biosignal enabled devices based on device usage, the cloud-enabled and artificial intelligence biosignal system comprising:

one or more biosignal enabled devices, each of the one or more biosignal enabled devices comprising a device processor and a device memory storing a first AI based coaching model, and each of the one or more biosignal enabled devices configured to collect biosignal data from respective users;

server computing instructions configured for execution on a cloud based server comprising a server processor and a server memory, wherein the cloud based server is communicatively coupled to the one or more biosignal enabled devices, wherein the server computing instructions, when executed by the server processor, cause the server processor to:

aggregate biosignal data as collected from respective users of the one or more biosignal enabled devices, train an enhanced AI based coaching model with the aggregated biosignal data as input as training data, wherein the enhanced AI based coaching model is configured to output one or more device usage classifications, and provide the enhanced AI based coaching model to the one or more biosignal enabled devices, wherein the enhanced AI based coaching model replaces or updates the first AI based coaching model in the device memory of the one or more biosignal enabled devices; and device computing instructions configured for execution by a respective device processor communicatively coupled to a biosignal enabled device of a user, the biosignal enabled device of the user comprising one of the one or more biosignal enabled devices, and wherein the device computing instructions as stored in a respective device memory of the biosignal enabled device of the user, when executed by the respective device processor, causes the respective device processor to:

receive user-specific biosignal data of the user, input the user-specific biosignal data into the enhanced AI based coaching model, wherein the enhanced AI based coaching model outputs a device usage classification, and initiate a coaching procedure based on the device usage classification, wherein the coaching procedure causes rendering of visual instructions on a display screen communicatively coupled to the biosignal enabled device of the user, wherein the visual instructions are provided to coach the user how to use or configure the biosignal enabled device of the user to implement an updated configuration for the biosignal enabled device of the user.

2. The cloud-enabled and AI based biosignal system of claim 1, wherein the server computing instructions, when executed by the server processor, cause the server processor to:

execute the enhanced AI based coaching model to detect one or more errors, wherein the one or more errors comprise one or more of: (1) when an output device usage classification fails to match an expected device usage classification selected from the one or more device usage classifications; or (2) when an output device usage classification fails to fall within one or more predetermined threshold values.

3. The cloud-enabled and AI based biosignal system of claim 1, wherein the biosignal enabled device of the user comprises a controller configured to control a prosthetic device, and wherein the device computing instructions, when executed by the respective device processor, further cause the respective device processor to:

calibrate the controller to control the prosthetic device based on the user-specific biosignal data of the user.

4. The cloud-enabled and AI based biosignal system of claim 1, wherein a performance metric indicating a performance improvement of the biosignal enabled device of the user is stored in the respective device memory of the biosignal enabled device of the user or the cloud based server.

5. The cloud-enabled and AI based biosignal system of claim 4, wherein the performance metric is rendered on the display screen.

6. The cloud-enabled and AI based biosignal system of claim 1, wherein at least one of the one or more biosignal enabled devices comprises a wearable device.

7. The cloud-enabled and AI based biosignal system of claim 1, wherein the device computing instructions, when executed by the respective device processor, further cause the respective device processor to:

graphically render the user-specific biosignal data of the user, as collected by the biosignal enabled device, with a second set of biosignal data as collected from at least one additional user.

8. The cloud-enabled and AI based biosignal system of claim 1, wherein the server computing instructions, when executed by the server processor, further cause the server processor to:

render, on a display screen of a computing device communicatively coupled to the cloud based server, a specialist portal comprising a specialist graphical user interface (GUI) configured to provide access to a medical professional to read, modify, or provide coaching instructions to the user via the display screen.

9. The cloud-enabled and AI based biosignal system of claim 8, wherein the specialist GUI comprises one or more options to adjust or configure operation of the biosignal enabled device of the user.

10. The cloud-enabled and AI based biosignal system of claim 1, wherein the respective device processor comprises one or more of: a local processor coupled with the biosignal enabled device; or a remote processor wirelessly connected to a computing device.

11. The cloud-enabled and AI based biosignal system of claim 9, wherein the specialist GUI is configured to launch a virtual meeting between the medical professional and the user.

12. The cloud-enabled and AI based biosignal system of claim 11, wherein the virtual meeting comprises at least one of:

providing, via the display screen, virtual instructions regarding set-up of the biosignal enabled device;

providing, via the display screen, the user-specific biosignal data of the user as collected by the biosignal enabled device;

providing, via the display screen, a comparison of the user-specific biosignal data of the user to a second set of biosignal data of at least one additional user;

modulating, by the respective device processor, one or more settings of the biosignal enabled device of the user;

providing, via the display screen, one or more suggestions for improving a performance of the biosignal enabled device of the user; or training, via the display screen, the user to improve a performance of the biosignal enabled device of the user.

13. The cloud-enabled and AI based biosignal system of claim 1, wherein the user-specific biosignal data of the user is stored in the respective device memory or the server memory as a user profile of the user.

14. The cloud-enabled and AI based biosignal system of claim 13, wherein the user profile receives a configuration update causing the biosignal enabled device to operate according to an improved operation configuration, and where the configuration update is provided by at least one of:

modification of configuration settings, by the user or a medical professional, of the biosignal enabled device; or modification of configuration settings, as automatically downloaded or transmitted from the cloud based server to the biosignal enabled device, for implementation by the biosignal enabled device.

15. A cloud-enabled and artificial intelligence (AI) based biosignal method for enhancing biosignal enabled devices based on device usage, the cloud-enabled and artificial intelligence biosignal method comprising:

aggregating, at a cloud based server comprising a server processor and a server memory, biosignal data as collected from respective users of one or more biosignal enabled devices, each of the one or more biosignal enabled devices comprising a device processor and a device memory storing a first AI based coaching model, and each of the one or more biosignal enabled devices configured to collect biosignal data from the respective users;

training an enhanced AI based coaching model with the aggregated biosignal data as input as training data, wherein the enhanced AI based coaching model is configured to output one or more device usage classifications;

providing the enhanced AI based coaching model to the one or more biosignal enabled devices, wherein the enhanced AI based coaching model replaces or updates the first AI based coaching model in the device memory of the one or more biosignal enabled devices;

receiving, at a biosignal enabled device of a user, user-specific biosignal data of the user, wherein the biosignal enabled device of the user comprises one of the one or more biosignal enabled devices;

inputting, at the biosignal enabled device of the user, the user-specific biosignal data into the enhanced AI based coaching model, wherein the enhanced AI based coaching model outputs a device usage classification; and initiating a coaching procedure based on the device usage classification, wherein the coaching procedure causes rendering of visual instructions on a display screen communicatively coupled to the biosignal enabled device of the user, wherein the visual instructions are provided to coach the user how to use or configure the biosignal enabled device of the user to implement an updated configuration for the biosignal enabled device of the user.

16. The cloud-enabled and AI based biosignal method of claim 15, further comprising:

executing the enhanced AI based coaching model to detect one or more errors, wherein the one or more errors comprise one or more of: (1) when an output device usage classification fails to match an expected device usage classification selected from the one or more device usage classifications; or (2) when an output device usage classification fails to fall within one or more predetermined threshold values.

17. The cloud-enabled and AI based biosignal method of claim 15, wherein the biosignal enabled device of the user comprises a controller configured to control a prosthetic device, and wherein the method further comprises:

calibrating the controller to control the prosthetic device based on the user-specific biosignal data of the user.

18. The cloud-enabled and AI based biosignal method of claim 15, further comprising:

rendering, on a display screen of a computing device communicatively coupled to the cloud based server, a specialist portal comprising a specialist graphical user interface (GUI) configured to provide access to a medical professional to read, modify, or provide coaching instructions to the user via the display screen.

19. A tangible, non-transitory computer-readable medium storing instructions for enhancing biosignal enabled devices based on device usage, that when executed by one or more processors cause the one or more processors to:

aggregate, at a cloud based server comprising a server processor and a server memory, biosignal data as collected from respective users of one or more biosignal enabled devices, each of the one or more biosignal enabled devices comprising a device processor and a device memory storing a first AI based coaching model, and each of the biosignal enabled devices configured to collect biosignal data from the respective users;

train an enhanced AI based coaching model with the aggregated biosignal data as input as training data, wherein the enhanced AI based coaching model is configured to output one or more device usage classifications;

provide the enhanced AI based coaching model to the one or more biosignal enabled devices, wherein the enhanced AI based coaching model replaces or updates the first AI based coaching model in the device memory of the one or more biosignal enabled devices;

receive, at a biosignal enabled device of a user, user-specific biosignal data of the user, wherein the biosignal enabled device of the user comprises one of the one or more biosignal enabled devices;

input, at the biosignal enabled device of the user, the user-specific biosignal data to the enhanced AI based coaching model, wherein the enhanced AI based coaching model outputs a device usage classification; and initiate a coaching procedure based on the device usage classification, wherein the coaching procedure causes rendering of visual instructions on a display screen communicatively coupled to the biosignal enabled device of the user, wherein the visual instructions are provided to coach the user how to use or configure the biosignal enabled device of the user to implement an updated configuration for the biosignal enabled device of the user.

20. The tangible, non-transitory computer-readable medium of claim 19, wherein the instructions, when executed by one or more processors, further cause the one or more processors to:

execute the enhanced AI based coaching model to detect one or more errors, wherein the one or more errors comprise one or more of: (1) when an output device usage classification fails to match an expected device usage classification selected from the one or more device usage classifications; or (2) when an output device usage classification fails to fall within one or more predetermined threshold values.

\* \* \* \* \*